(12) United States Patent
Davis et al.

(10) Patent No.: US 11,262,841 B2
(45) Date of Patent: Mar. 1, 2022

(54) WIRELESS WRIST COMPUTING AND CONTROL DEVICE AND METHOD FOR 3D IMAGING, MAPPING, NETWORKING AND INTERFACING

(71) Applicant: eyeCam LLC, San Francisco, CA (US)

(72) Inventors: Bryan Jonathan Davis, San Francisco, CA (US); James Fisher, Walnut Creek, CA (US); Ronald Eugene Fisher, San Francisco, CA (US); Walter Norman Maclay, Sunnyvale, CA (US); Stuart Gregory Tyrrell, Los Altos, CA (US)

(73) Assignee: eyeCam LLC, San Francisco, CA (US)

( * ) Notice: Subject to any disclaimer, the term of this patent is extended or adjusted under 35 U.S.C. 154(b) by 0 days.

(21) Appl. No.: 15/633,286

(22) Filed: Jun. 26, 2017

(65) Prior Publication Data
US 2018/0129284 A1 May 10, 2018

Related U.S. Application Data

(63) Continuation of application No. 14/070,425, filed on Nov. 1, 2013, now Pat. No. 9,690,376.
(Continued)

(51) Int. Cl.
*G06F 3/01* (2006.01)
*A61B 5/11* (2006.01)
(Continued)

(52) U.S. Cl.
CPC .......... *G06F 3/014* (2013.01); *A61B 5/0261* (2013.01); *A61B 5/1125* (2013.01);
(Continued)

(58) Field of Classification Search
CPC .............. G06F 3/011; G06F 11/3485; G06F 17/30424; G06F 17/30554; G06F 1/163;
(Continued)

(56) References Cited

U.S. PATENT DOCUMENTS 580,726 A 4/1897 Scheid
591,372 A 10/1897 Rasmussen
(Continued)

FOREIGN PATENT DOCUMENTS

AU 2011213036 B2 11/2013
CN 1711516 A 12/2005
(Continued)

OTHER PUBLICATIONS

International Search Report dated Mar. 27, 2014 issued on International Patent Application PCT/US2013068167, filed Nov. 1, 2013, 2 pages.
(Continued)

*Primary Examiner* — Kent W Chang
*Assistant Examiner* — Scott D Au
(74) *Attorney, Agent, or Firm* — Franklin & Associates International Inc; Matthew F. Lambrinos

(57) ABSTRACT

An apparatus and method for light and optical depth mapping, 3D imaging, modeling, networking, and interfacing on an autonomous, intelligent, wearable wireless wrist computing, display and control system for onboard and remote device and graphic user interface control. Embodiments of the invention enable augmentation of people, objects, devices and spaces into a virtual environment and augmentation of virtual objects and interfaces into the physical world through its wireless multimedia streaming and multi-interface display and projection systems.

39 Claims, 25 Drawing Sheets

Related U.S. Application Data

(60) Provisional application No. 61/796,056, filed on Nov. 1, 2012.

(51) Int. Cl.
  *A61B 5/00* (2006.01)
  *G06F 3/03* (2006.01)
  *A61B 5/026* (2006.01)
  *A61B 5/021* (2006.01)
  *A61B 5/024* (2006.01)

(52) U.S. Cl.
  CPC ............ *A61B 5/1128* (2013.01); *A61B 5/681* (2013.01); *G06F 3/017* (2013.01); *G06F 3/0304* (2013.01); *A61B 5/021* (2013.01); *A61B 5/024* (2013.01); *A61B 2562/0219* (2013.01)

(58) Field of Classification Search
  CPC ...... G06F 1/1686; G06F 3/023; G06F 3/0325; G06F 3/0421; G06F 3/0428; G06F 3/04815; G06F 3/0487; G06F 9/54
  See application file for complete search history.

(56) References Cited

U.S. PATENT DOCUMENTS

| | | | |
|---|---|---|---|
| 3,541,541 A | 11/1970 | Engelbart | |
| 5,807,267 A | 9/1998 | Bryars et al. | |
| 5,913,727 A * | 6/1999 | Ahdoot ............... | A63F 13/06 345/156 |
| 6,005,548 A | 12/1999 | Latypov et al. | |
| 6,647,632 B2 | 11/2003 | Tominaga et al. | |
| 6,747,632 B2 | 6/2004 | Howard | |
| 6,771,294 B1 * | 8/2004 | Pulli ................. | G06F 3/017 715/863 |
| 6,778,850 B1 * | 8/2004 | Adler ................. | A61B 6/12 600/427 |
| 6,898,517 B1 | 5/2005 | Froeberg | |
| 7,298,360 B2 * | 11/2007 | Howard ............... | G06F 3/014 345/158 |
| 8,018,579 B1 | 9/2011 | Krah | |
| 8,228,315 B1 | 7/2012 | Starner et al. | |
| 8,292,833 B2 | 10/2012 | Son | |
| 8,320,621 B2 | 11/2012 | McEldowney | |
| 8,390,821 B2 | 3/2013 | Shpunt et al. | |
| 8,670,029 B2 | 3/2014 | McEldowney | |
| 8,717,291 B2 | 5/2014 | Sun et al. | |
| 8,749,557 B2 * | 6/2014 | Evertt ................ | G06F 3/011 345/473 |
| 8,787,663 B2 | 7/2014 | Litvak et al. | |
| 9,019,267 B2 * | 4/2015 | Gurman ............... | H04N 13/204 345/419 |
| 9,047,698 B2 | 6/2015 | Maciocci et al. | |
| 9,080,977 B2 * | 7/2015 | Contag .............. | G01N 21/6428 |
| 9,582,889 B2 | 2/2017 | Shpunt et al. | |
| 9,690,376 B2 * | 6/2017 | Davis ................ | G06F 3/014 |
| 10,061,387 B2 | 8/2018 | Toney et al. | |
| 2002/0024500 A1 | 2/2002 | Howard | |
| 2004/0036717 A1 | 2/2004 | Kjeldsen et al. | |
| 2004/0239640 A1 | 12/2004 | Lahade | |
| 2005/0041016 A1 | 2/2005 | Howard | |
| 2006/0238502 A1 | 10/2006 | Kanamori | |
| 2007/0052672 A1 | 3/2007 | Ritter et al. | |
| 2009/0046140 A1 * | 2/2009 | Lashmet ............. | G09G 3/002 348/51 |
| 2009/0096783 A1 | 4/2009 | Shpunt | |
| 2010/0110264 A1 * | 5/2010 | Carroll .............. | H04N 9/3194 348/333.01 |
| 2010/0289655 A1 | 11/2010 | Dickie | |
| 2011/0022033 A1 | 1/2011 | Guzman | |
| 2011/0025827 A1 | 2/2011 | Shpunt et al. | |
| 2011/0066324 A1 | 3/2011 | Odland | |
| 2011/0080339 A1 | 4/2011 | Sun et al. | |
| 2011/0190612 A1 | 8/2011 | McKenna et al. | |
| 2011/0211754 A1 | 9/2011 | Litvak et al. | |
| 2011/0248963 A1 * | 10/2011 | Lawrence ............. | G06F 3/042 345/175 |
| 2012/0212399 A1 | 8/2012 | Border et al. | |
| 2012/0214544 A1 | 8/2012 | Shivappa | |
| 2012/0249409 A1 * | 10/2012 | Toney ............... | G06F 1/163 345/156 |
| 2012/0249741 A1 | 10/2012 | Maciocci et al. | |
| 2013/0013229 A1 * | 1/2013 | Norieda ............. | G06F 3/01 702/56 |
| 2014/0028980 A1 | 1/2014 | Othmer | |
| 2014/0055352 A1 | 2/2014 | Davis et al. | |
| 2014/0125583 A1 | 5/2014 | Aoki et al. | |
| 2014/0358281 A1 | 12/2014 | Lipton et al. | |
| 2015/0222842 A1 | 8/2015 | Kwong | |
| 2015/0227164 A1 | 8/2015 | Laycock | |
| 2015/0332075 A1 * | 11/2015 | Burch .............. | G06F 1/163 345/156 |
| 2016/0184639 A1 | 6/2016 | Bentley et al. | |
| 2017/0123487 A1 | 5/2017 | Hazra et al. | |

FOREIGN PATENT DOCUMENTS

| | | |
|---|---|---|
| CN | 101702103 A | 5/2010 |
| CN | 101882012 A | 11/2010 |
| CN | 102124423 A | 7/2011 |
| CN | 102129152 A | 7/2011 |
| CN | 102231037 A | 11/2011 |
| CN | 101496033 B | 3/2012 |
| CN | 102387344 A | 3/2012 |
| CN | 105027030 B | 10/2018 |
| CN | 109799900 A | 5/2019 |
| EP | 2403234 A1 | 1/2012 |
| EP | 3654146 A1 | 5/2020 |
| EP | 2915025 B8 | 6/2021 |
| JP | 1007899 B2 | 11/2007 |
| JP | 2011146835 A | 7/2011 |
| JP | 1988016 B2 | 8/2012 |
| JP | 5155448 B2 | 2/2015 |
| JP | 5672862 B2 | 2/2015 |
| KR | 20090061179 A | 6/2009 |
| KR | 20100047793 A | 5/2010 |
| KR | 101284797 B1 | 7/2013 |
| KR | 101302138 B1 | 8/2013 |
| KR | 101691633 B1 | 1/2017 |
| KR | 102065687 B1 | 2/2020 |
| RU | 2339087 C2 | 11/2008 |
| TW | 528881 B | 4/2003 |
| WO | 1998007129 A1 | 2/1998 |
| WO | 2009093461 A1 | 7/2009 |
| WO | 2011013079 A1 | 2/2011 |
| WO | 2011097291 A1 | 8/2011 |
| WO | 2014071254 A1 | 5/2014 |
| WO | 2019079790 | 4/2019 |

OTHER PUBLICATIONS

Written Opinion dated Mar. 26, 2014 issued on International Patent Application PCT/US2013068167, filed Nov. 1, 2013, 4 pages.
International Search Report dated Feb. 27, 2019 issued on International Patent Application No. PCT/US2018/056858, filed Oct. 22, 2018 in the name of EyeCam, Inc.
International Written Opinion dated Apr. 25, 2019 issued on International Patent Application No. PCT/US2018/056858, filed Oct. 22, 2018 in the name of EyeCam, Inc.
EPO Text Intended For Grant dated Oct. 23, 2020 issued on on EP13850844, filed Jan. 11, 2013, in the name of EyeCam, LLC.
Written submissions dated Sep. 15, 2020 on EP13850844, filed Jan. 11, 2013, in the name of EyeCam, LLC.
Annex to EPO examination report dated Jul. 3, 2018 issued on n EP13850844, filed Jan. 11, 2013, in the name of EyeCam, LLC.
European Search Report issued Oct. 5, 2016 on EP13850844, filed Jan. 11, 2013, in the name of EyeCam, LLC.
Amendments submitted Apr. 27, 2017 to EPO before European Examination of EP13850844, filed Jan. 11, 2013, in the name of EyeCam, LLC.

(56) References Cited

OTHER PUBLICATIONS

Annex to EPO Summons dated May 18, 2020 to attend oral proceedings on EP13850844, filed Jan. 11, 2013, in the name of EyeCam, LLC.
Written submissions dated 13 Auguust 2020 in reply to Annex to EPO Summons dated May 18, 2020 to attend oral proceedings on EP13850844, filed Jan. 11, 2013, in the name of EyeCam, LLC.
EPO Communication under R71(3) EPC Intention to Grant dated Oct. 23, 2020 issued on EP Application 13850844.5.
Annex to EPO communication dated Aug. 17, 2020 from the Examining Division issued on EP Application 13850844.5.
Chris HarrisonHrvoje Benkoandrew D. Wilson, Omnitouch: Wearable Multitouch Interaction Everywhere, UST11, Oct. 16-19, 2011, Santa Barbara, CA USA.
Amendment filed Dec. 27, 2017 at Korean Intellectual Property Office on (KR 20170003713 A, KR 102065687 B1) filed Nov. 1, 2013 in the name of Eyecam, LLC.
Notification of Reason of Refusal dated Dec. 27, 2018 from Korean Intellectual Property Office issued on (KR 20170003713 A, KR 102065687 B1) filed Nov. 1, 2013 in the name of Eyecam, LLC.
Reply filed Jun. 24, 2019 at Korean Intellectual Property Office on (KR 20170003713 A, KR 102065687 B1) filed Nov. 1, 2013 in the name of Eyecam, LLC.
Amendment filed Jan. 20, 2020 at at Korean Intellectual Property Office on (KR 20170003713 A, KR 102065687 B1) filed Nov. 1, 2013 in the name of Eyecam, LLC.
Grant of Patent Communication dated Oct. 4, 2019 from Korean Intellectual Property Office issued on (KR 20170003713 A , KR 102065687 B1) filed Nov. 1, 2013 in the name of Eyecam, LLC.
Office Action dated Dec. 16, 2019 from Indian Intellectual Property Office issued on Patent Application No/1565/KOLNP/2015 filed Nov. 1, 2013 in the name of Eyecam, LLC.
Reply filed Sep. 15, 2020 at ndian Intellectual Property Office on Patent Application No/ 1565/KOLNP/2015 filed Nov. 1, 2013 in the name of Eyecam, LLC.

\* cited by examiner

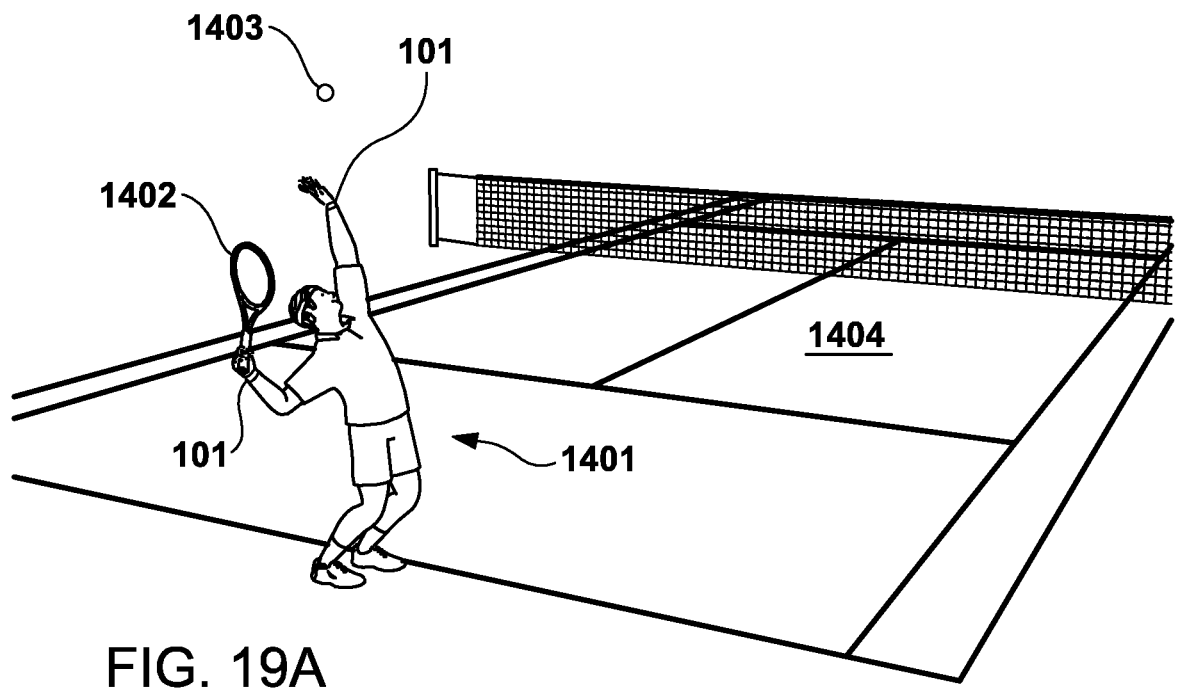
FIG. 19A
FIG. 19B
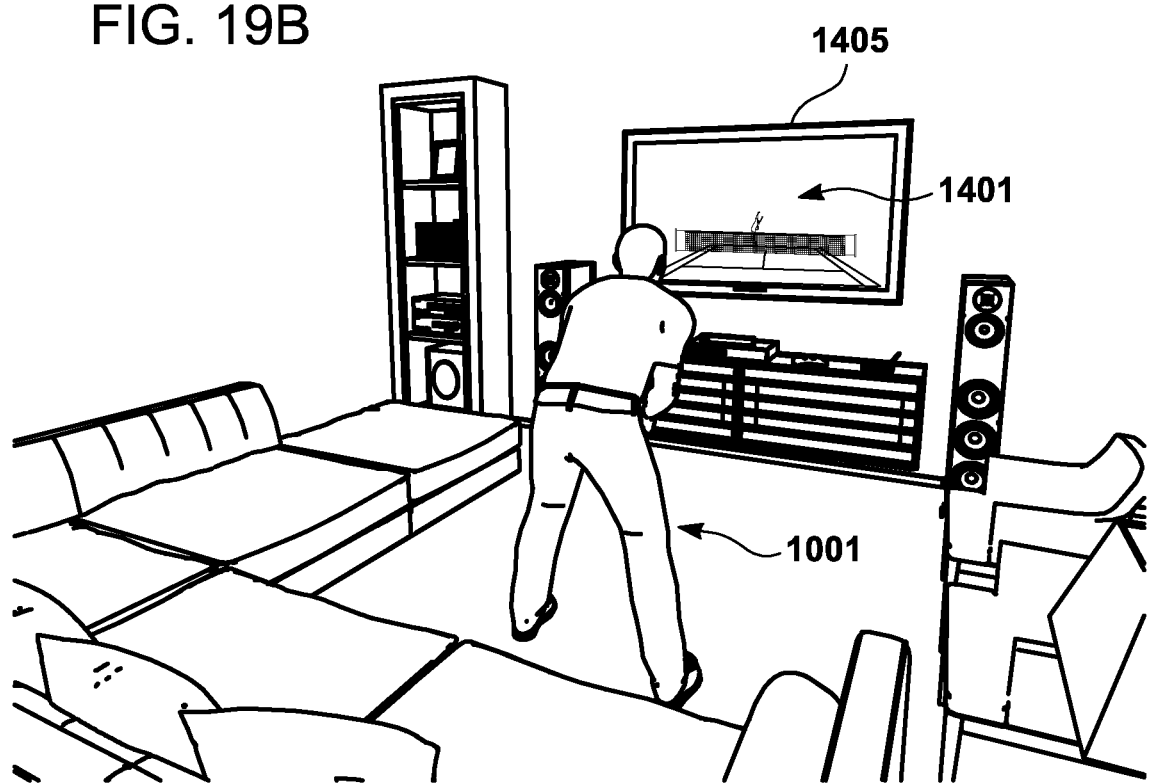

WIRELESS WRIST COMPUTING AND CONTROL DEVICE AND METHOD FOR 3D IMAGING, MAPPING, NETWORKING AND INTERFACING

CROSS REFERENCE TO RELATED APPLICATIONS

This application is a Continuation of U.S. patent application Ser. No. 14/070,425, filed 1 Nov. 2013, which claims priority from U.S. Provisional Application No. 61/796,056, filed 1 Nov. 2012, wherein each are incorporated herein in its entirety by this reference thereto.

TECHNICAL FIELD

This invention relates to the field of wearable computing. More particularly, the invention relates to devices and methods for 3D mapping, imaging, networking, communications, and multi-interface remote controlling.

DESCRIPTION OF RELATED ART

Existing control devices include the early mouse technology in the form of hand-held wired x-y positional input devices, such as found in U.S. Pat. No. 3,541,541, to sensor and spatial positioning systems such as U.S. Pat. No. 6,005,548, to wearable optical hand, finger and object spatial positioning systems that incorporate gesture and voice recognition and touchscreen interfacing controls.

Prior art such as U.S. Pat. No. 6,647,632 introduced a wireless control device worn on the wrist with light emitters and sensors placed on the inside of the hand to identify the position of the users hand and fingers, recognize pre-assigned gestures and voice commands and relay the data to a controlled device and U.S. Pat. No. 8,292,833 B2 introduced a wrist worn Finger Motion Detecting Apparatus that uses optical and ultrasonic wave signal monitoring of the wearers tendons to identify the position and movement of their hand and fingers and relay data to a controlled device. U.S. Patent Application Pub. No. 2009/0096783 A1 introduces an indoor three dimensional structured imaging system and body motion and gesture interfacing system using a light speckle pattern to 3D map illuminated objects and U.S. Patent Pub. Application No. 2011/0025827 introduces stereoscopic depth mapping using a combination of light projection and 3D color imaging, both systems are limited to depth mapping, modeling and interfacing from a fixed location.

A common attribute of the mouse and other handheld and wearable interfacing devices is the definition of the controllers being peripheral devices, and a positional data input accessories to remote controlled devices and computing systems. Therefore, there are many problems with the known with existing technology.

SUMMARY OF THE INVENTION

An apparatus and method for light and optical depth mapping, 3D imaging, modeling, networking, and interfacing on an autonomous, intelligent, wearable wireless wrist computing, display and control system for onboard and remote device and graphic user interface control. Embodiments of the invention enable augmentation of people, objects, devices, and spaces into a virtual environment and augmentation of virtual objects and interfaces into the physical world through its wireless multimedia streaming and multi-interface display and projection systems.

BRIEF DESCRIPTION OF THE DRAWINGS

FIGS. 19A and 19B are perspective views of a professional tennis player wearing a wrist console.

DETAILED DESCRIPTION

Figure 1A:
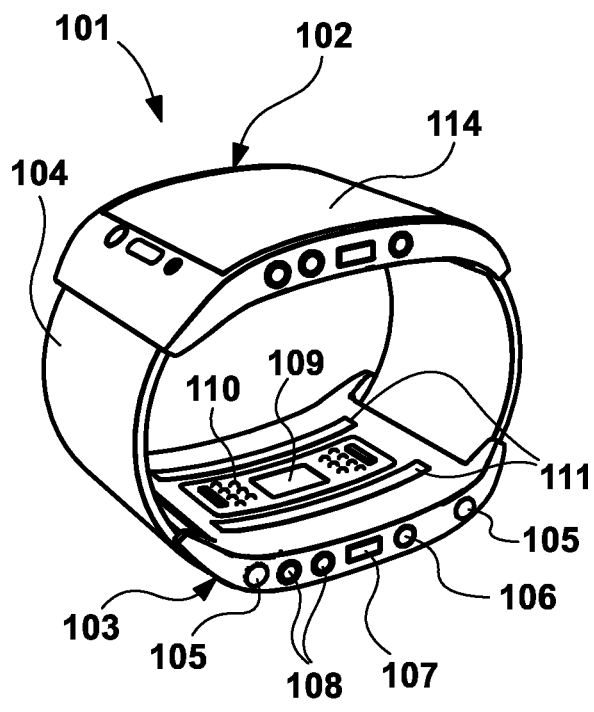
FIG. 1A is a perspective view of an embodiment of the wrist console.

Apparatus and methods are described for autonomous, intelligent wearable wireless voice, data, and video communications systems that combine onboard computing with a multi-interface wrist console, remote device and graphic user interface (GUI) controller. Apparatus and methods are also described for 3 Dimensional (3D) optical hand, body, object, sensor, and environment imaging, mapping, modeling, networking, and interfacing. Further, apparatus and methods are described for enabling augmentation of real world people, objects, and devices into a virtual environment and for enabling augmentation of virtual objects and interfaces into a physical environment.

Apparatus and methods are described that are advancements in wearable computing optics and interfacing over prior art, expanding from hand, finger, and object positioning to a 3D scanning, mapping, modeling, imaging, projection, and wireless interfacing systems all captured, rendered, and operated by a wrist computing and control console.

Apparatus and methods are described implementing a combination of light emitters; and sensors including body, motion, orientation, and location sensors. These apparatus and methods may further include optic, stereoscopic, or plenoptic lens arrays to generate depth maps and 3D imaging models, as well as virtual computing, interfacing and networking platforms by dynamically scanning and imaging the hands, body, objects and environment, indoors or outdoors in daylight or at night using one or more depth measurement and imaging methods.

Further, apparatus and methods are described for mobile light and optical depth mapping imaging, modeling, networking, and interfacing on an autonomous, intelligent wearable wireless wrist computing, display, and control system for onboard and remote device and graphic user interface (GUI) control. Augmentation of real world people, objects, and devices into a virtual environment and augmentation of virtual objects, interfaces, and environments into the real world through wireless multimedia streaming and multi-interface display and projection system is also described.

Light Mapping

Embodiments of the invention involve incorporating narrow or wide beam light emitters, or a structured light imaging system on the top and bottom of wrist consoles worn by a user. In embodiments, a device scans the top and bottom of the hand and fingers, the body, and any objects in the hand or in the field of the light imaging system.

When using narrow or wide beam emitter and sensor arrays, the emitter array may be assigned to move the focal point of the light beams up and down and back and forth across an x and y axis grid formation during the scanning process and are then assigned fixed positions to monitor hand and finger motion. The emitters form an x-y array for detecting the hand and fingers in the x and y dimensions of space and the sensors detect the presence or absence of a reflection. In embodiments, the depth (z) distance is measured by triangulation of the light beam reflection off of the target surface to the light sensor either mapping the target surface depth when the light beams are in motion and the object is stationary or dynamically identifying the position of the scanned object when the light beams are fixed and the scanned object is in motion.

In embodiments using a structured light imaging system light emitters and diffusers are incorporated to produce a light speckle pattern across the top and bottom of the hand and cover surrounding objects and environment. In embodiments designated camera sensors on a wrist console recognize the light speckle pattern and the directional reflection of each dot off of the target surface land on a different pixel within the camera sensor to triangulate the beam of light and determine the position, depth, and shape of the target surface.

Stationary structured light imaging system provides a constant point of origin for the projected light pattern with the only variables being the position, depth, and surface shape of target objects in its projection field. A wrist console introduces a wearable structured light imaging system that at most times is in motion. Even when a person holds their arm and hand steady, slight body movements can alter both the position and direction of the light emitters and projected light pattern and consequently the position and line of sight of the camera sensors.

In embodiments, the light mapping system is used both for initial mapping and modeling of the hand, body, objects, and environment and to dynamically monitor hand, finger, body, and object motion for gesture interfacing and control and to perform instant keyless user verification and authorization upon device sign-in, as well as performing instant user verification for payment and other secure transactions and security related functions such as keyless entry to home and vehicles and access to unique user accounts and user specific functions and applications on the device.

Position and Orientation Mapping

In embodiments, it is necessary to incorporate constant motion, position, and orientation data. When light and optical depth mapping and 3D color imaging is performed, the spatial position, directional motion, and orientation of the wrist console is acquired by any combination of onboard accelerometers, altimeters, compasses, and gyroscopes, as well as GPS and radio frequency (RF) directional signal and location data to continuously identify the precise relational position of the wrist console cameras, light emitters, and sensors to reflected and imaged surfaces to assign that data to each light point and color pixel in a depth and color map.

Optical Mapping and Imaging

In embodiments, depth mapping and 3D imaging is achieved using a stereoscopic or plenoptic multi-lens arrays. These arrays enable a wrist console's top and bottom modules to dynamically capture 3D or 4D multi-depth of field color imaging of the hand, body, surrounding objects, and environment.

In embodiments, when incorporating one or more stereoscopic lens arrays a wrist console performs stereo triangulation by determining the depth of two or more focal points in the scene, and determining the depths of the corresponding points in other images by matching points and features in one image to corresponding points and features in other images. To overcome the correspondence problem, the stereoscopic imaging system may select to incorporate the light imaging system to project one or more points of light on a target surface enabling the imaging system to verify the precise corresponding points in the images. Once the corresponding points have been identified, the imaging system determines the focal depths of all other points in the scene.

In embodiments, when incorporating a light-field plenoptic micro-lens array the wrist console captures multiple depths of field simultaneously. While stereoscopic lens arrays are limited to two or more individual lens arrays and sensors, each capturing light and color from a single depth of field, necessitating corresponding image analysis to match points in two or more images, the plenoptic micro-lens array assigns multiple lenses to a single sensor and captures the light and color from the entire field of view, while each lens captures a different depth of field enabling the camera to assign depth to all points in a captured image.

In embodiments, the optical imaging system is used both for initial imaging, depth and color mapping, and modeling of the hand, body, objects, and environment and to dynamically image hand, finger, body, and object motion for gesture and projection interfacing, to perform user verification and authorization and other security related functions, and to capture video and live stream user activities in 2D and 3D or 4D video and perform other imaging applications.

Modeling and Rigging

After light scanning and 3D imaging an object, the corresponding depth map is converted to a point cloud, a map of vertices with corresponding vectors in which each point is assigned an x, y and z (depth) coordinate. This process turns a grey scale depth map generated by the light scanning process or a 3D imaging of an object into a vertex in which each point or pixel in the image is identified as an x, y, and z coordinate that can be converted into metric units.

In embodiments, when a light scanned depth map is converted to a vertex and vector map by identifying the precise depth and directional position of each surface point, the color mapping process is enabled in which corresponding depth mapped color pixels are assigned to each point on the 3D vertex and vector map. This process converts the point cloud into a mesh in which points on a contiguous surface are connected and determines, for example, that one finger is behind the other, and they are not a single surface. The grid follows the surface shape, texture, and contours of the 3D mapped object.

Converting a surface mesh and 3D map of a persons hand or body into a functional character model that can be animated to mirror the movements of the wearer, incorporates a process of mapping the persons joints and assigning joint positions to the matching areas on the 3D model and generating an internal model rigging similar to the skeletal structure in the human body. Then attaching the rigging to the 3D mesh and model and assigning areas of influence to the mesh and surface of the 3D model similar to the effect of muscles and tendons on body motion and the skin.

In embodiments, when an existing functional character rigging exists, rather than generating a rig for each new model, the existing rig is scaled and conformed to the dimensions, shape, and physical characteristics of the mapped person. This may incorporate a program for determining body flexibility and motion based on the body type, sex, size, weight, age, health, fitness, flexibility, and other parameters of the mapped person to more accurately conform the rig and model to mimic the natural body motion and mobility of the person.

During the 3D light mapping and imaging process the wrist console may prompt the wearer to perform a number of hand and body motions, gestures, and positions to identify the joints, bone structure and mobility of the person. This may necessitate capturing multiple 3D scans and images of the person and then adjusting the rigging to replicate the precise body structure and mobility.

Sensor Mapping and Interfacing

In embodiments a wrist console is used to continuously map full body motion in real-time and incorporates external sensors into its 3D mapping and interfacing system. This includes body, clothing and remote wireless equipment sensors.

By attaching micro sensors to the body or clothing on each of the limbs and joints or networking with embedded sensors in clothing, shoes and equipment the wrist console can identify the spatial position of one or more wireless sensors and assign those sensors to the mapped 3D model of the person, equipment and environment.

In embodiments the wrist console may use one or a combination of networking methods including Radio Frequency (RF), light/IR, Near Field Communication (NFC), Bluetooth, WiFi and Cellular networks for local and remote sensors and devices interfacing and control. This sensor network enables both sending and receiving data by the wrist console for wireless operation and control of remote sensors and dynamic mapping, interfacing and streaming of networked data as well as onboard or remote storage of mapped data.

In embodiments when the wrist console operates as a sensor hub for a wireless sensor network (WSN), the wrist console networks with each sensor directly or via a mesh network in which each sensor operates as a node and not only captures and sends data but also serves as a relay passing data on to the other nodes in the network.

In embodiments when monitoring body motion by identifying the 3D position, velocity, and acceleration of each joint or body part, a complete Cartesian coordinate 3D model of the body may be described mathematically with distance coordinates of x, y, and z; velocity coordinates of $v_x$, $v_y$, and $v_z$; and acceleration coordinates of $a_x$, $a_y$, and $a_z$ to calculate the future position of an object in motion. Once the wrist console has identified and networked with the individual sensors or mesh sensor group, the wrist console is able to map the precise position of the sensors on the 3D character model. This process enables the wrist console to capture full body motion and acceleration as a continuous data stream and assign that data to the 3D rigged virtual model of the wearer to provide a real-time animation of the body and full body interfacing in a virtual environment.

In embodiments when the wrist console is used to map the internal body anatomy and interface with internal body sensors, devices and prosthetics, the wrist console incorporates a similar method of mapping, modeling, networking and interfacing with the internal body as it does with the external body. In embodiments when the wrist console is mapping the external body using the light and optical mapping and external sensors the wrist console is also performing internal mapping which incorporate the wrist console's onboard health and body sensors and then expands to all networked internal body sensors including ingested and implanted sensors, devices, prosthetics and any body or brain machine interfacing systems.

In embodiments the wrist console incorporates onboard body health and fitness sensors including top and bottom module wrist facing Infrared (IR) spectroscopy and pulse oximeter, heart rate monitor, thermometer, galvanic response system, Electroencephalograph (EEG), Electrocardiograph (ECG), Electromyograph (EMG), and glucose meter.

Projection Mapping and Interfacing

In embodiments, incorporating a pico projector for projecting an image onto external surfaces, the light and image mapping systems and orientation system are used to depth map surfaces, dynamically map the spatial position of the hands and fingers and the relational position of the wrist console and projector to a target surface. These processes enable the wrist console to map a projected display and graphic user interface onto any surface. The light and optical mapping systems are also used to dynamically monitor hand and finger motions and gestures enabling the user to perform touch and gesture interfacing to control the projected interface.

Further embodiments include an active touch screen displays, microphones, speakers, tactile feedback (haptic) sensor arrays, and front facing video cameras. These embodiments enable touch, voice, and gesture interfacing and voice command, video conferencing, and dynamic touch screen display with onboard graphic user interfaces.

In embodiments, the wrist console incorporates a touch screen display, one or more microphones and speakers, and tactile feedback (haptic) sensor array. These embodiments provide touch, voice, and gesture interfacing options for the user, enabling the user to select the most effective method for displaying and interfacing with a graphic user interface either on the wrist console or on one or more networked devices.

In embodiments, the user can map or assign a specific user interface such as voice command or gesture interfacing to a specific function, application, or device. For example, if the user is using the wrist console to interfacing with a personal computer and a television the user may assign voice command to the television while using gesture and touch on the computer.

In embodiments, the wrist console incorporates haptic sensor strips and/or a ring of haptic sensors on the inside of both the top and bottom wrist units. The wrist console generates very intricate positional, vibrational, and pressure responses to minute finger, hand, wrist, and body movements. The tactile response may also be incorporated into gesture command, touch screen, and device controls and other user interface applications to simulate button press on a projected keyboard, or provide a tactile response and more realism to object and/or application selection and control in a virtual 2D or 3D environment. The haptic response system may also be used to indicate an incoming or outgoing call, text or other event, locational and/or relational distance to a recognized object or person or any other assigned contextual application, alarm or monitored health status event such as alerting the wearer when their heart rate rises above a designated rate or glucose levels fall above or below a designated level or to inform the wearer of a potential oncoming seizure. Different types of vibrational and/or electro-stimulated responses may be generated and assigned to different callers, events and applications.

Device Mapping and Interfacing

In embodiments, the wrist console is capable of streaming content that is stored and playing on the device and or streaming to the wrist controller from the Internet to the screens of one or more networked devices and/or streaming multimedia content from a networked TV, game console, PC, or other networked device to one or more other devices or displays. This peer-to-peer networking, content management, distribution, and streaming can be achieved using a number of different wireless networks. Some of those include WiFi, Bluetooth, cellular, Infrared/light, Radio Frequency (RF), and NFC for rapid payments and transactions. One method for connecting all displays and devices in its field of view is through a single WiFi peer-to-peer network where each device is connected wirelessly through a multichannel WiFi direct connect platform operating as a standalone WiFi hotspot and router, the wrist controller creates an ad-hoc peer-to-peer network with one or more wireless and/or Internet enabled devices and operates as remote wearable video game and computing console and wireless hub. The wrist console may also use any combination of networks to communicate with one or more devices.

In embodiments, the wrist console manages content across multiple networked devices and monitors based on the position of the display in the room and the relation of the display to the wrist console and user. The wrist console is able to connect with multiple devices using multiple methods, networks, and channels.

Detailed Overview of the Embodiments in the Drawings

FIG. 1A is a perspective view of an embodiment of the wrist console 101 depicting the top wrist module 102 and bottom wrist module 103 which serve as housing modules for internal components of the device. The wrist modules are connected with adjustable wrist straps 104 which in embodiments contain communication cables between the two wrist modules. The device further has a wrist strap release and locking system 105, forward facing light emitters 106 and sensors 107, and multi-camera lens array 108. FIG. 1A shows the inside view of the bottom module body sensors including light emitters and sensors 109, Galvanic Skin Response System (GSR) 110, and haptic feedback arrays (haptic array) 111, a partial view of the display 114, microphones 115, speakers 116, and top facing cameras 117.

Figure 1B:
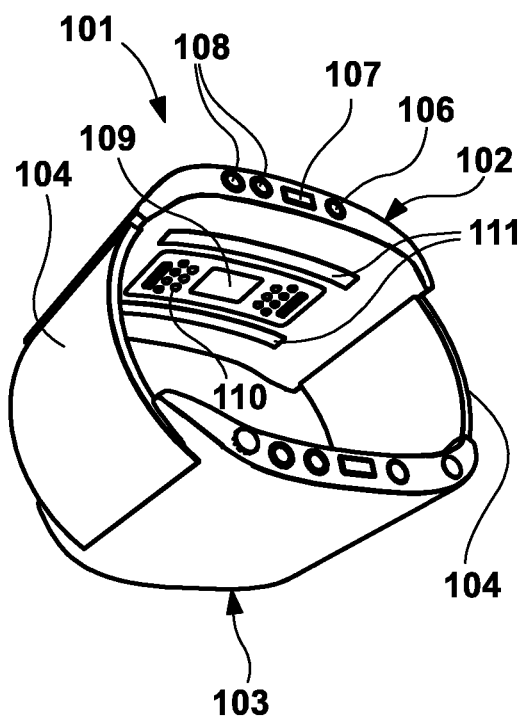
FIG. 1B is a perspective view of the embodiment shown in FIG. 1A.

FIG. 1B is a perspective view of the embodiment shown in FIG. 1A depicting a view of the top module 102 body sensors including light emitters and sensors 109, GSR 110 and Haptic Array 111.

Figure 1C:
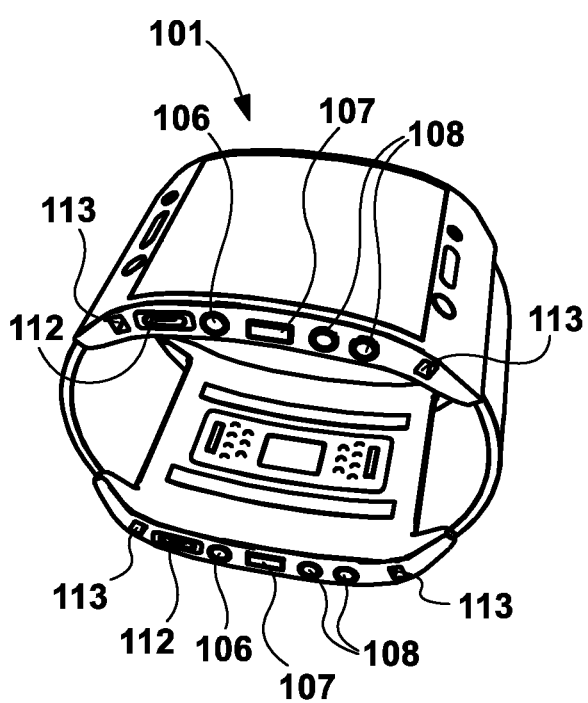
FIG. 1C is a perspective view of the embodiment shown in FIG. 1A.

FIG. 1C is a perspective view of the embodiment shown in FIG. 1A depicting an overhead view of the rear facing light emitters 106 and sensors 107, rear multi-camera lens array 108, power and data ports 112 and docking ports 113.

Figure 1D:
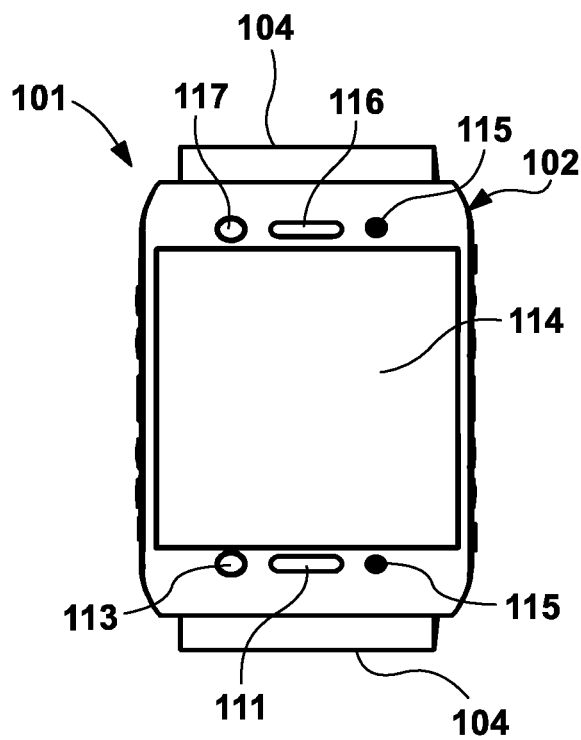
FIG. 1D is a top plan view of the embodiment shown in FIG. 1A.

FIG. 1D is a top plan view of the embodiment shown in FIG. 1A depicting the display 114, microphones 115, speakers 116 and top facing cameras 117.

Figure 2A:
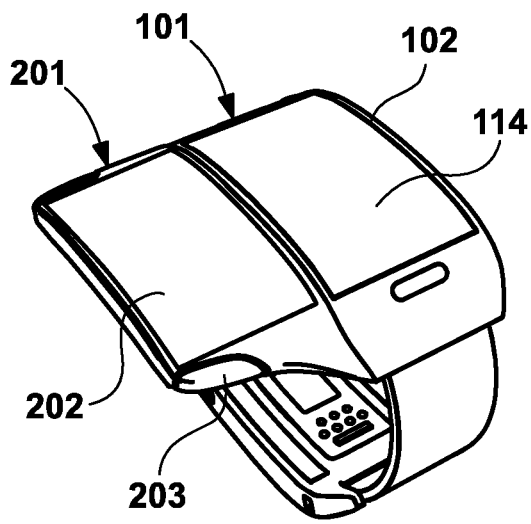
FIG. 2A is a perspective view of the embodiment shown in FIG. 1A depicting an expansion module.

FIG. 2A is a perspective view of the embodiment shown in FIG. 1A depicting an expansion module 201 with display 202 and release buttons 203, attached to the top module 102 of the wrist console 101. This expansion module may serve as an additional power and data storage, processing and/or communication system for the device and/or an expanded display and interfacing system and may also perform expanded services such as a plug in glucose meter or other application.

Figure 2B:
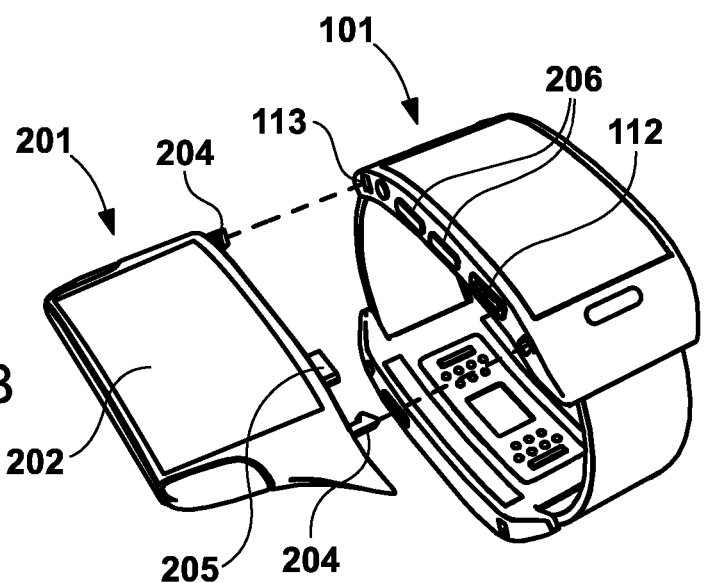
FIG. 2B is a perspective view of the embodiment shown in FIG. 1A depicting the detached expansion module.

FIG. 2B is a perspective view of the embodiment shown in FIG. 1A depicting the detached expansion module 201 with release buttons docking tabs 204 and power and data plug 204 and a button array 206 on the rear of the top module 102.

Figure 2C:
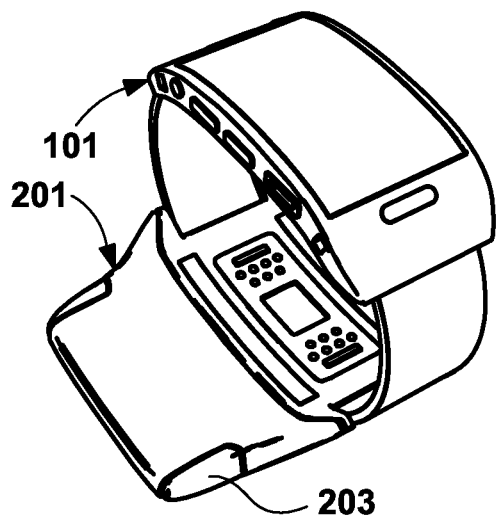
FIG. 2C is a perspective view of the embodiment shown in FIG. 1A depicting an expansion.

FIG. 2C is a perspective view of the embodiment shown in FIG. 1A depicting an expansion module 201 attached to the bottom module 103.

Figure 2D:
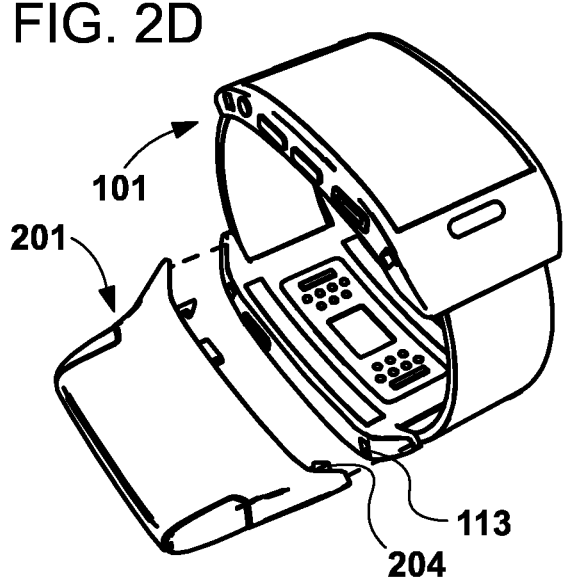
FIG. 2D is a perspective view of the embodiment shown in FIG. 1A with the expansion module detached.

FIG. 2D is a perspective view of the embodiment shown in FIG. 1A with an expansion module 201 detached from the bottom module 103.

FIGS. 3A-3L are perspective views illustrating a wrist console 101 performing depth mapping and 3D imaging the hand and fingers 301, identifying the joints and then rigging a fully functional computer model of the hand (hand model) 307.

Figure 3A:
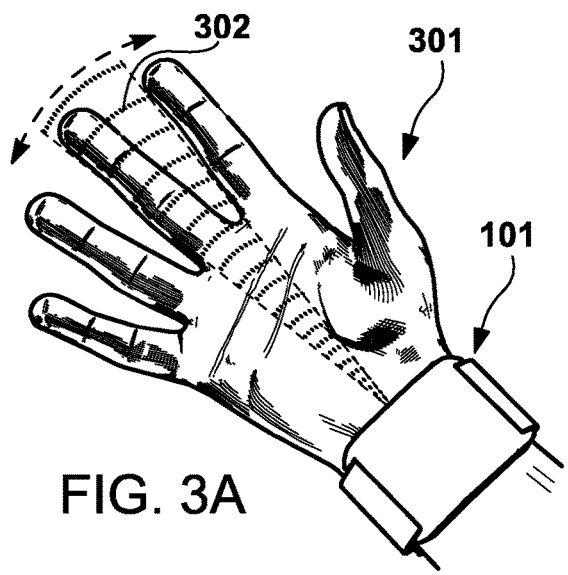
FIGS. 3A and 3B are perspective views illustrating an embodiment of the wrist console that incorporates one or more moving beams of light.
Figure 3B:
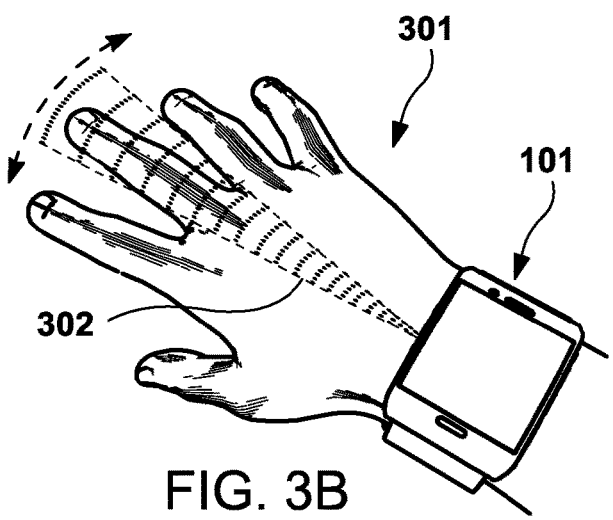

FIGS. 3A and 3B are perspective views illustrating an embodiment of the wrist console 101 that incorporates one or more moving beams of light 302 performing a light scan of the top and bottom of the hand and fingers 301 as a method for depth mapping. Triangulation is determined by the wrist console 101 light emitters 104 and sensors 106 as the light beams 302 move vertically and horizontally across the face of both sides of the hand and fingers 301.

Figure 3C:
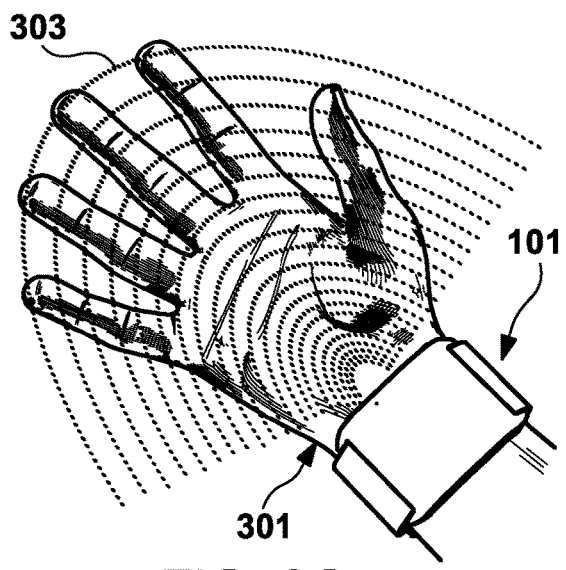
FIGS. 3C and 3D are perspective views depicting an embodiment of the invention that incorporates structured light imaging.
Figure 3D:
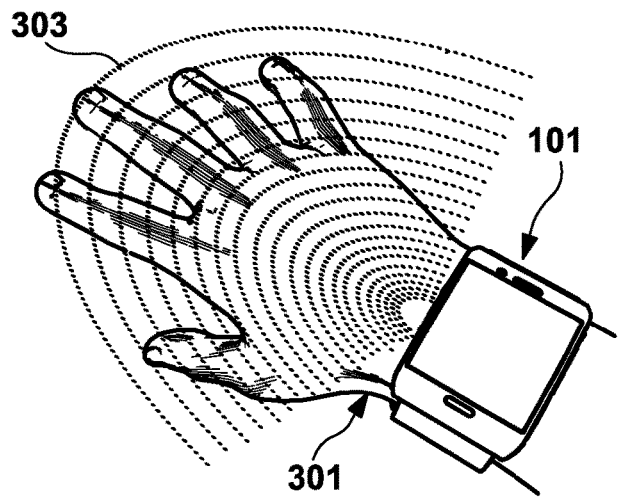

FIGS. 3C and 3D are perspective views depicting another embodiment of the invention that incorporates structured light imaging 303 into its depth mapping process by illuminating the top and bottom of the hand and fingers 301 with a speckled light pattern to light map 303 the entire hand 301 at once.

Figure 3E:
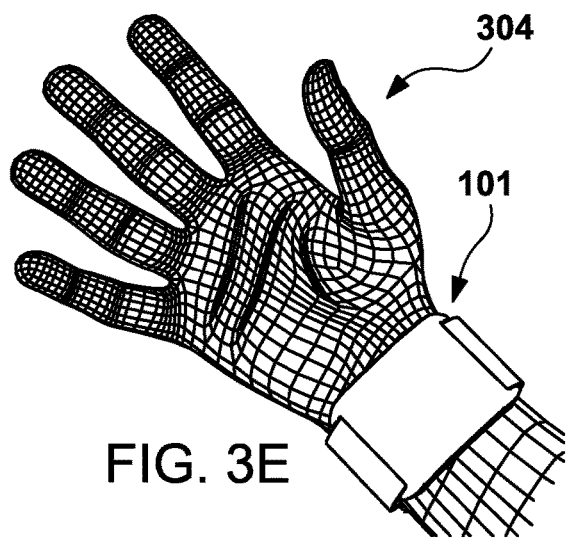
FIGS. 3E and 3F are perspective views illustrating a wrist console generating a depth and color mapped hand.
Figure 3F:
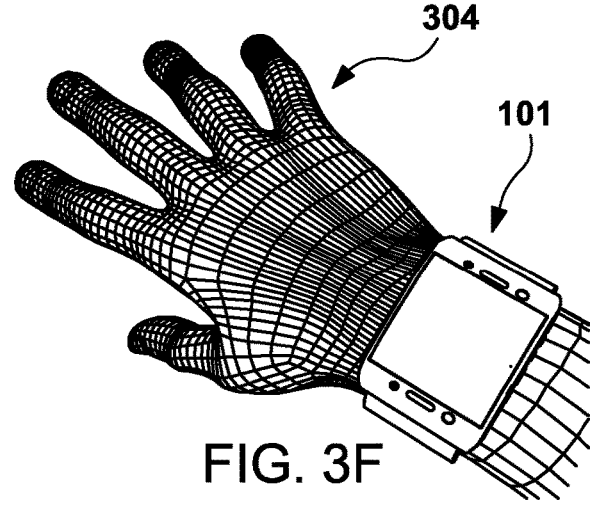

FIGS. 3E and 3F are perspective views illustrating the wrist console 101 generating a depth and color mapped hand 304 performing a combination of light mapping and imaging using 3D cameras 108 or 4D imaging using a plenoptic multi-lens array cameras 108 on both the top module and bottom of the wrist console 101.

Figure 3G:
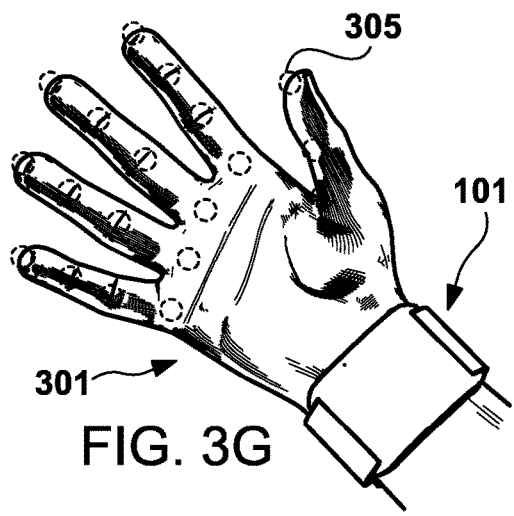
FIGS. 3G and 3H are perspective views illustrating a wrist console identifying the precise position of joints and creases of the hand.
Figure 3H:
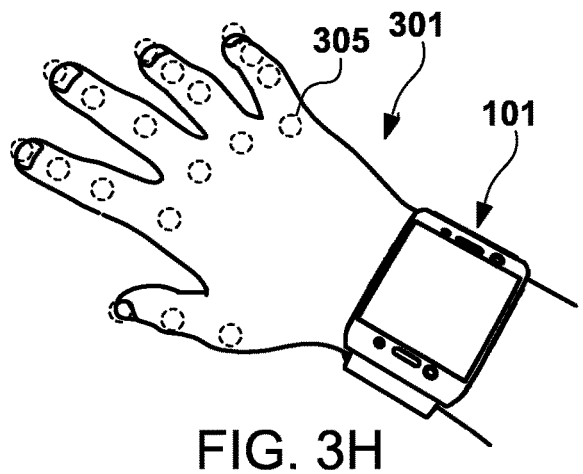

FIGS. 3G and 3H are perspective views illustrating the wrist console 101 identifying the precise position of joints and creases 305 on the top and bottom of the hand and fingers 301 for the purpose of generating a rig for the 3D mapped hand 304.

Figure 3I:
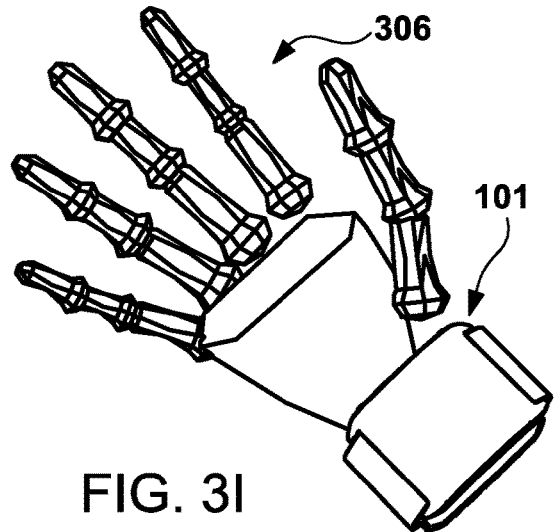
FIGS. 3I and 3J are perspective views illustrating a wrist console generating a functional rigging of the hand.
Figure 3J:
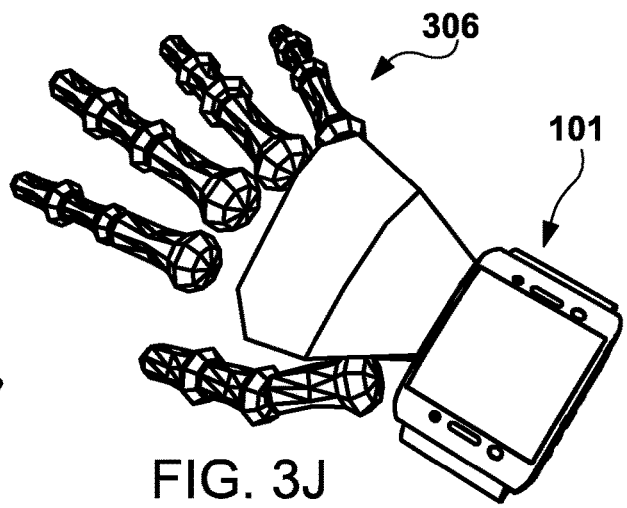

FIGS. 3I and 3J are perspective views illustrating the wrist console 101 generating a functional rigging of the hand (hand rig) 306 from the top and bottom perspective.

Figure 3K:
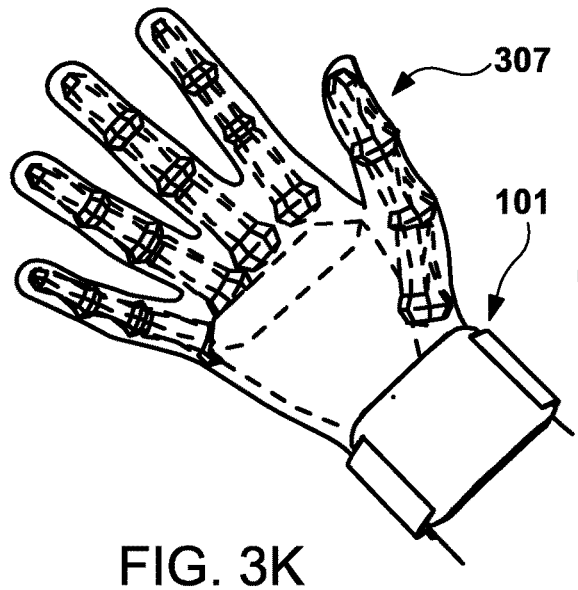
FIGS. 3K and 3L are perspective views illustrating an embodiment incorporating a hand rig into the 3D mapped hand.
Figure 3L:
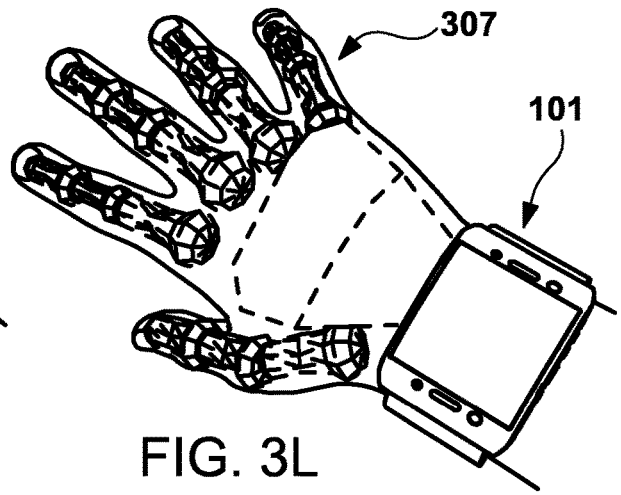

FIGS. 3K and 3L are perspective views illustrating the invention incorporating the hand rig 306 into the 3D mapped hand 304 to create a fully functional rigged computer model of the hand (hand model) 307 capable of being animated and replicating the movements of the users hand and fingers 301 in real-time.

FIGS. 4A-4F and FIGS. 5A and 5B are perspective views illustrating an application of the invention where the user performs and selects control functions for different gestures. The wrist console 101 assigns those controls to the hand model 307, which is used to carry out the users gesture inputs and commands in a 2D or 3D computing environment. FIGS. 4A-4F and FIGS. 5A and 5B represent only a few examples of gesture interfacing control options for a potentially limitless custom interface programming system.

Figure 4A:
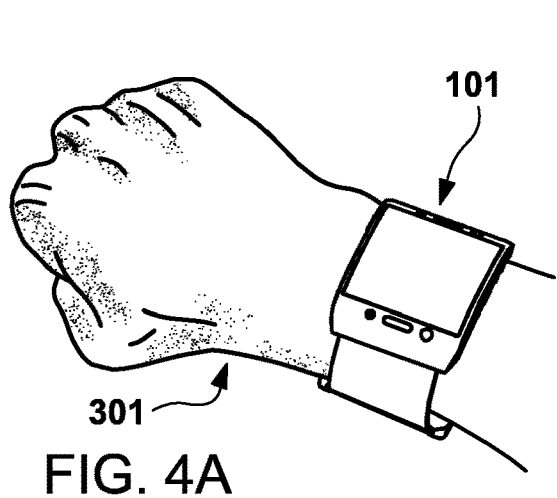
FIGS. 4A and 4B are perspective views illustrating the user's hand and fingers used to combine a gesture with a motion.
Figure 4B:
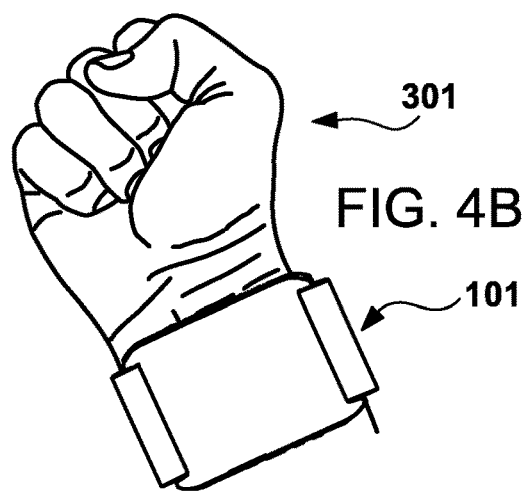

FIGS. 4A and 4B are perspective views illustrating the user's hand and fingers 301 used to combine a gesture (making a fist) with a motion (turning and moving the wrist) to a assign a customized gesture interface control function. The gesture is mapped and recorded by the wrist console 101.

Figure 4C:
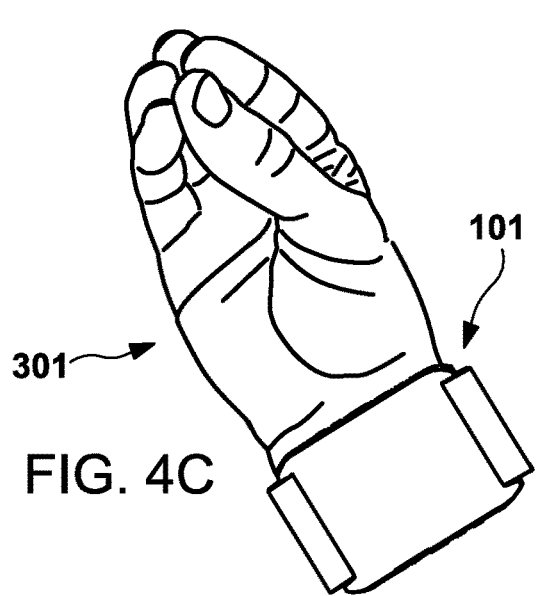
FIG. 4C is a perspective view illustrating the user using performing and selecting a gesture interface control function that involves multiple fingers.

FIG. 4C is a perspective view illustrating the user using performing and selecting a gesture interface input and control function that involves multiple fingers 301.

Figure 4D:
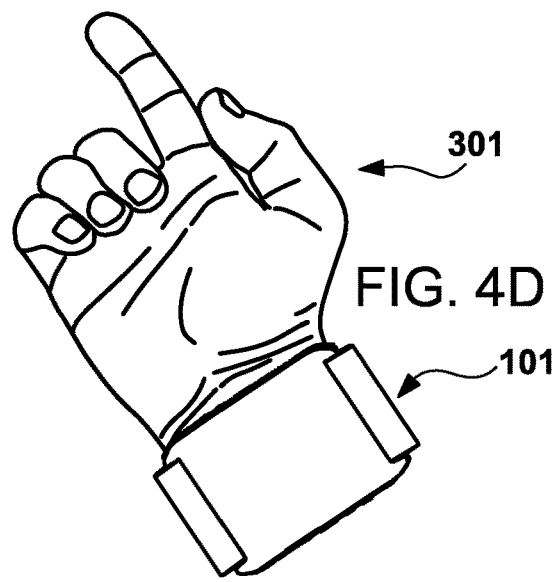
FIG. 4D is a perspective view illustrating the user performing and selecting a gesture interface control function that involves one finger.

FIG. 4D is a perspective view illustrating the user performing and selecting a gesture interface control function that involves one finger 301.

Figure 4E:
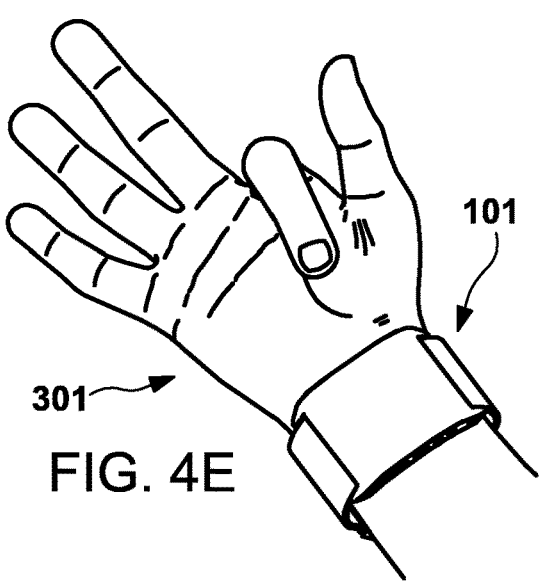
FIG. 4E is a perspective view illustrating the user performing and selecting a gesture interface control that involves touching a specified finger to an identified point or area on the hand.

FIG. 4E is a perspective view illustrating the user performing and selecting a gesture interface control that involves touching a specified finger to an identified point or area on the hand 301.

Figure 4F:
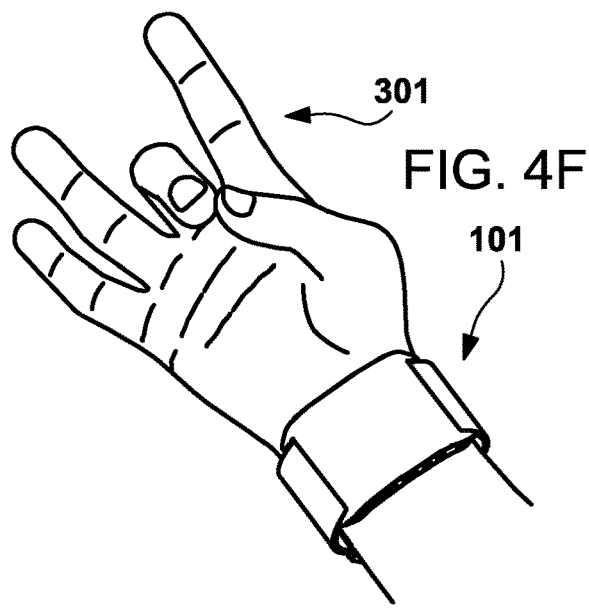
FIG. 4F is a perspective view illustrating the user performing and selecting a gesture interface control function that involves touching one specified finger to another specified finger.

FIG. 4F is a perspective view illustrating the user performing and selecting a gesture interface control function that involves touching one specified finger to another specified finger 301.

Figure 5A:
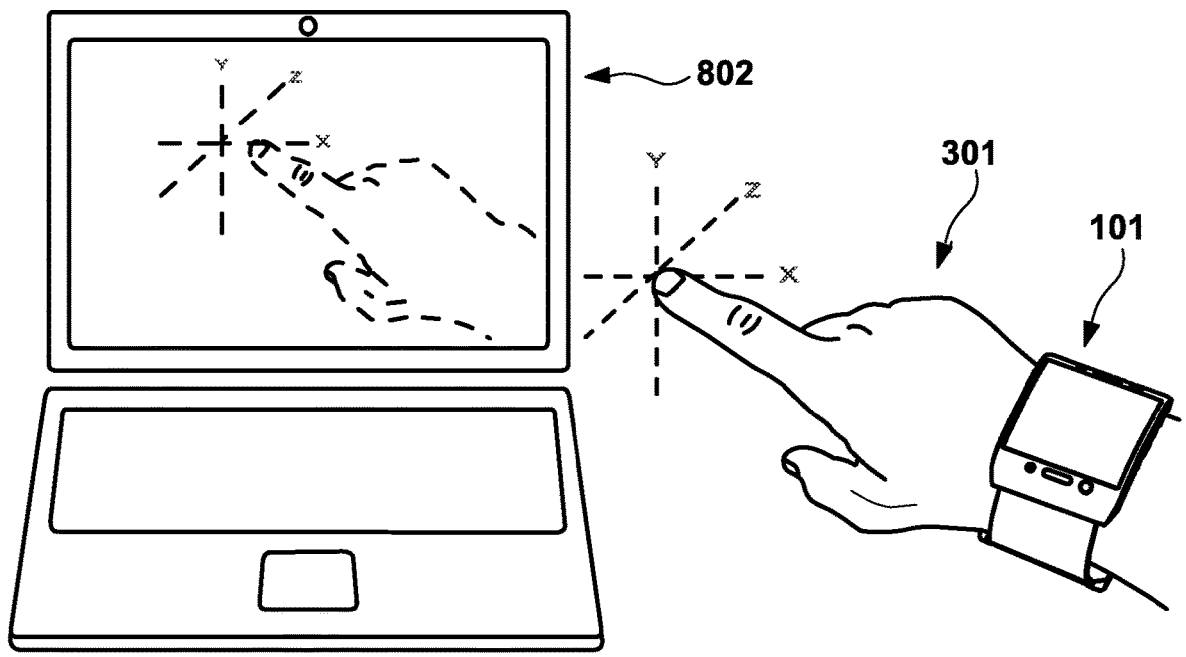
FIG. 5A is a perspective view illustrating a single point of control for a 2D or 3D computing environment on an external networked device using a single finger as a controller.

FIG. 5A is a perspective view illustrating a single point of control for a 2D or 3D computing environment on an external networked device 802 using a single finger as a controller 301.

Figure 5B:
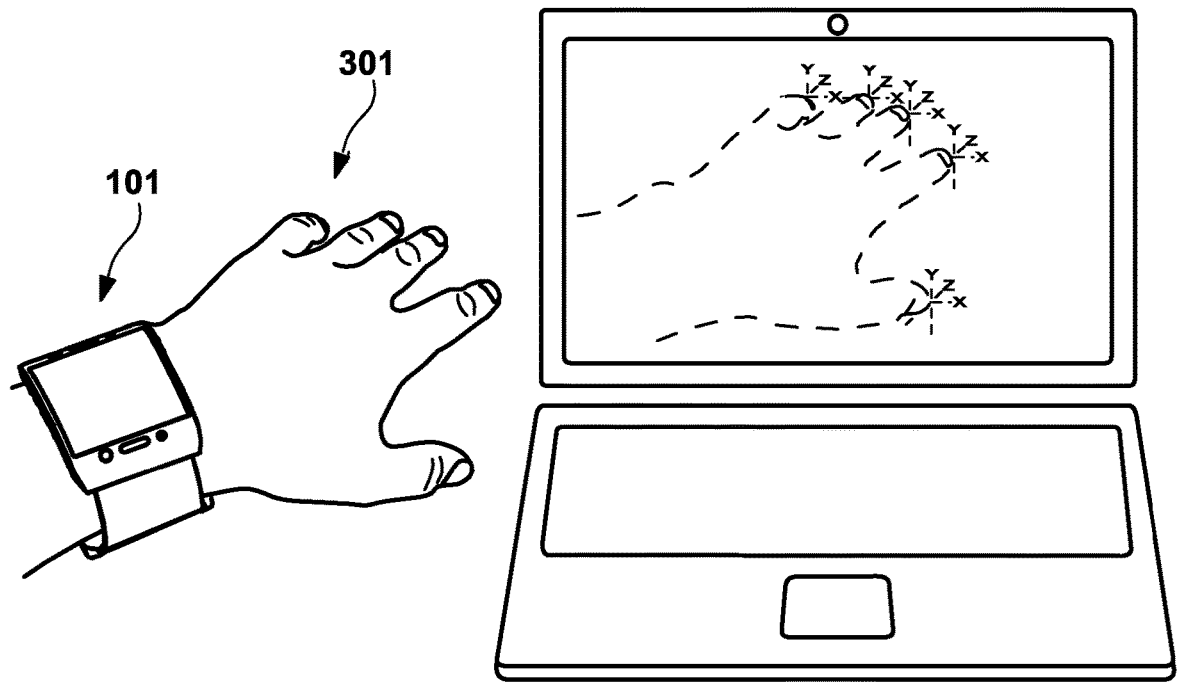
FIG. 5B is a perspective view illustrating multiple points of control for a 2D or 3D computing environment on an external networked device using multiple fingers as controllers.

FIG. 5B is a perspective view illustrating multiple points of control for a 2D or 3D computing environment on an external networked device 802 using multiple fingers as controllers 301.

Figure 6A:
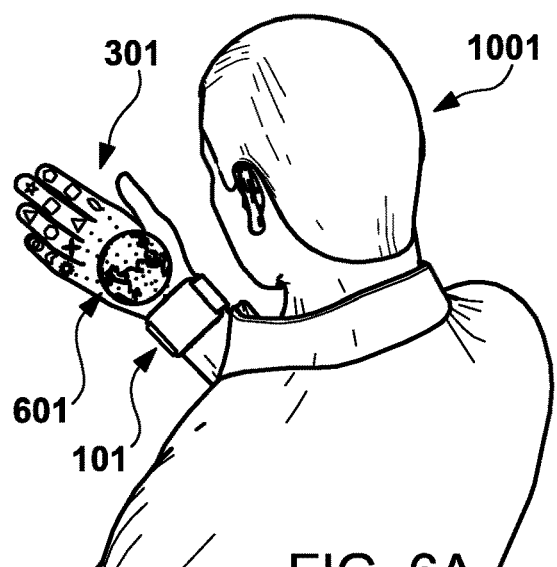
FIG. 6A is a perspective view illustrating a wrist console projecting a graphic user interface (GUI) onto the user's hand and fingers.

FIG. 6A is a perspective view illustrating the wrist console 101 projecting a graphic user interface (GUI) 601 on to the user's hand and fingers 301. The projected interface is mapped onto the hand using the light mapping and 3D imaging system.

Figure 6B:
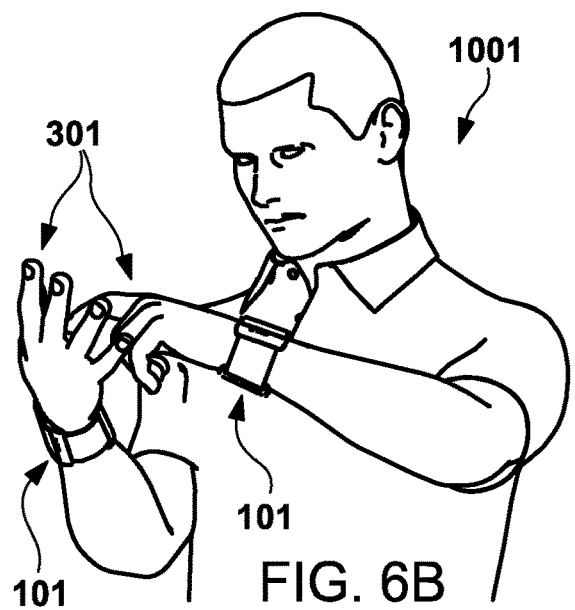
FIG. 6B is a perspective view illustrating a user performing touch and gesture interfacing to control a projected GUI on the user's hand and fingers.

FIG. 6B is a perspective view illustrating a user performing touch and gesture interfacing to control a projected GUI 601 on the user's hand and fingers 301.

Figure 6C:
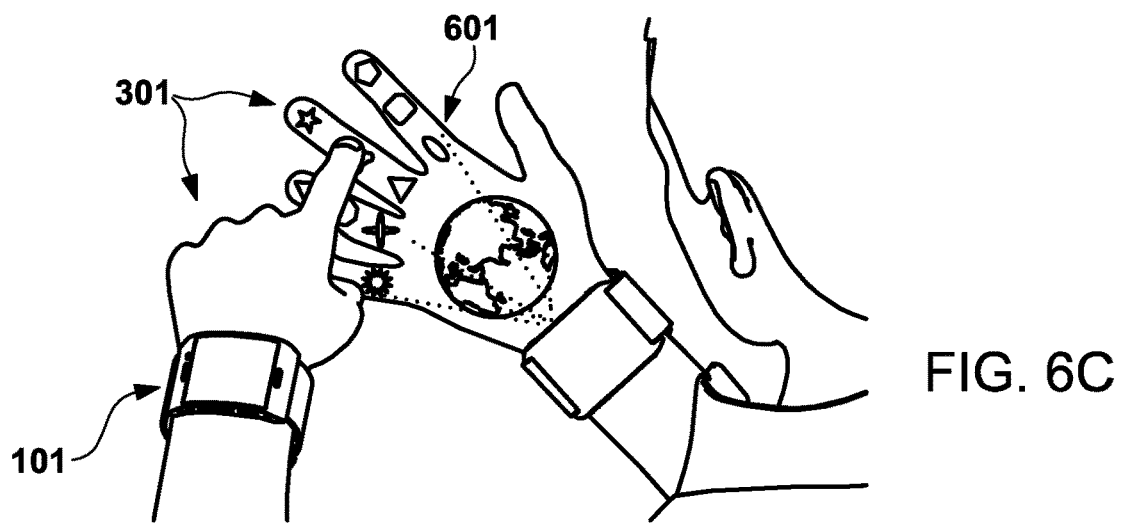
FIG. 6C is a perspective view illustrating a wrist console projecting a graphic user interface onto the users hands and fingers.

FIG. 6C is a perspective view illustrating the wrist console 101 projecting a graphic user interface 601 onto the users hands and fingers. In FIG. 6C the user has spread out their hand and fingers and the projected interface has dynamically conformed to the new position of the hand and fingers 301. The user is selecting one of the projected icons representing an active program or application running on wrist console 101 or remotely via an Internet connection.

Figure 6D:
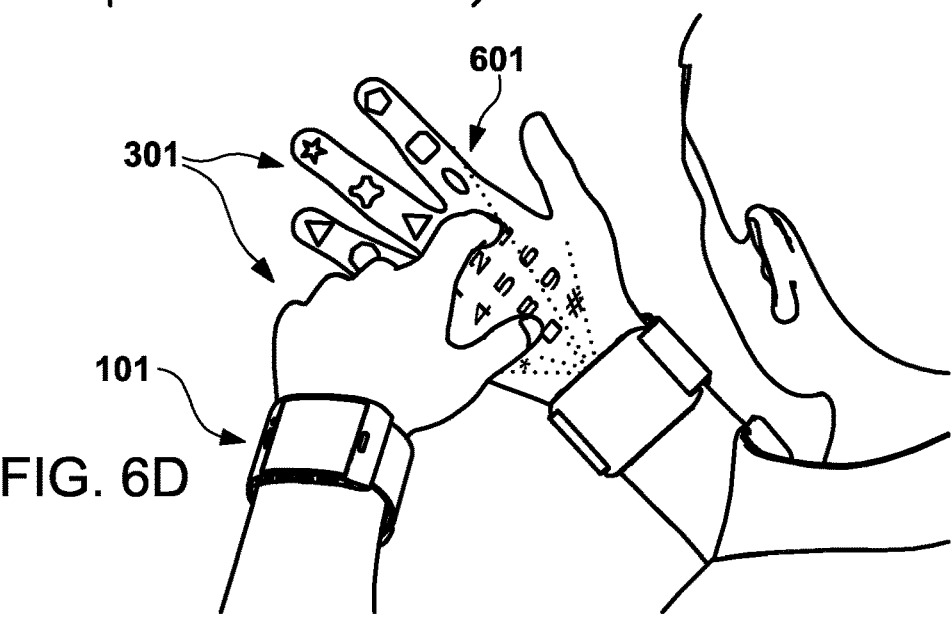
FIG. 6D is a perspective view illustrating the user typing on a projected keypad on the users hand.

FIG. 6D is a perspective view illustrating the user typing on a projected keypad 601 on the users hand 301.

Figure 7:
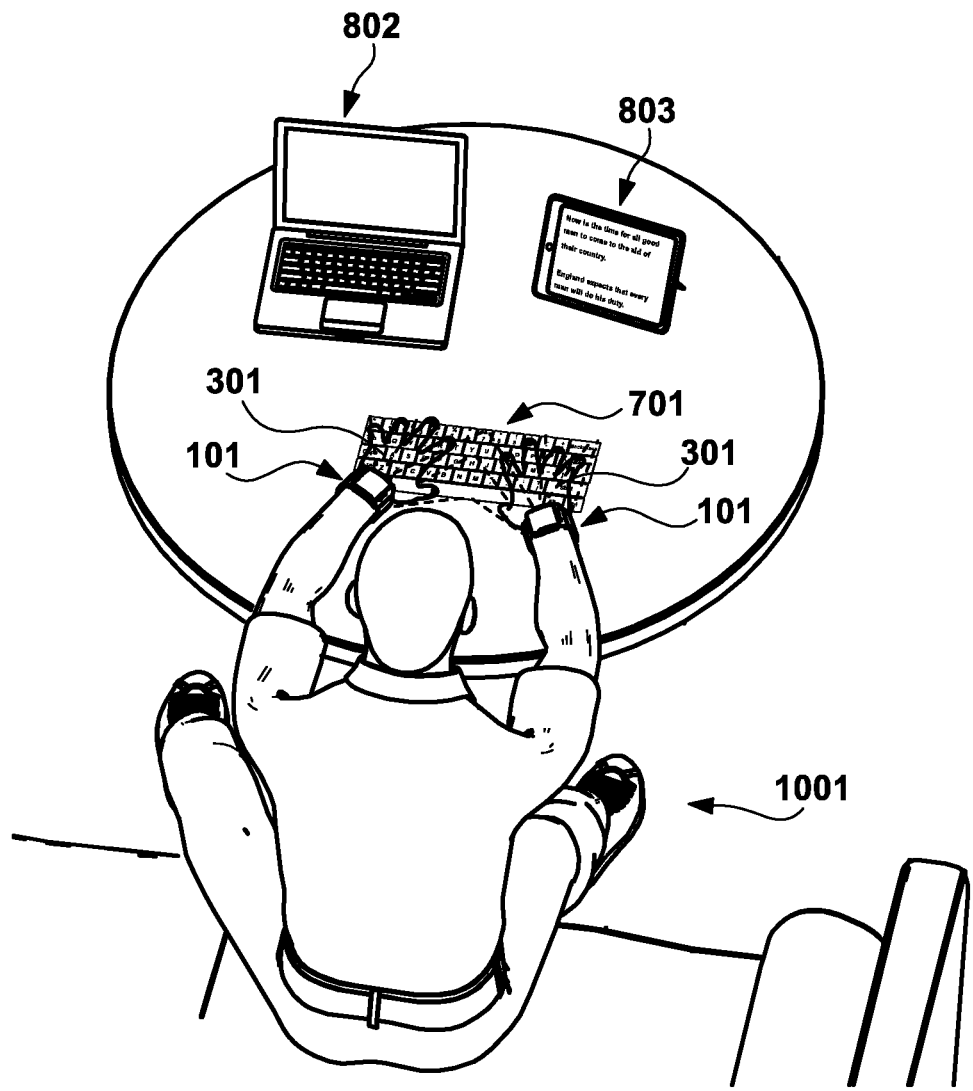
FIG. 7 is a perspective view illustrating a user typing on a projected keyboard mapped on to an external surface by both a left and right wrist console

FIG. 7 is a perspective view illustrating a user typing on a projected keyboard 701 mapped on to an external surface by both a left and right wrist console 101. FIG. 7 depicts an embodiment with a coordinated dual projected interface in which both left and right wrist consoles operate in concert in mapping and projecting a dynamic interface on a projected surface. FIG. 7 depicts the user typing a document on the projected keyboard that is displayed on an external device 803. The left and right wrist consoles are either operating as a single input device and relaying data wirelessly to a remote control device 803 or the wrist consoles 101 are operating as primary operating and control device and streaming data to a remote display 803.

Figure Sets 8A-8D and 9A and 9B are perspective views depicting the wrist console wirelessly interfacing with external devices. In each of the figures the wrist console 101 is shown on both wrists, although a pair of consoles may be operated as a single device or device pair, each wrist console 101 may also operate autonomously and does not need a second console to perform two handed gesture interface control. A single wrist console 101 is capable of monitoring a second hand in close proximity for dual hand interfacing or may operate in concert with a second wrist console 101 enabling expanded functionality such as multi-function two-handed control, dual projection, expanded networking, processing, interfacing, power and data storage.

Figure 8A:
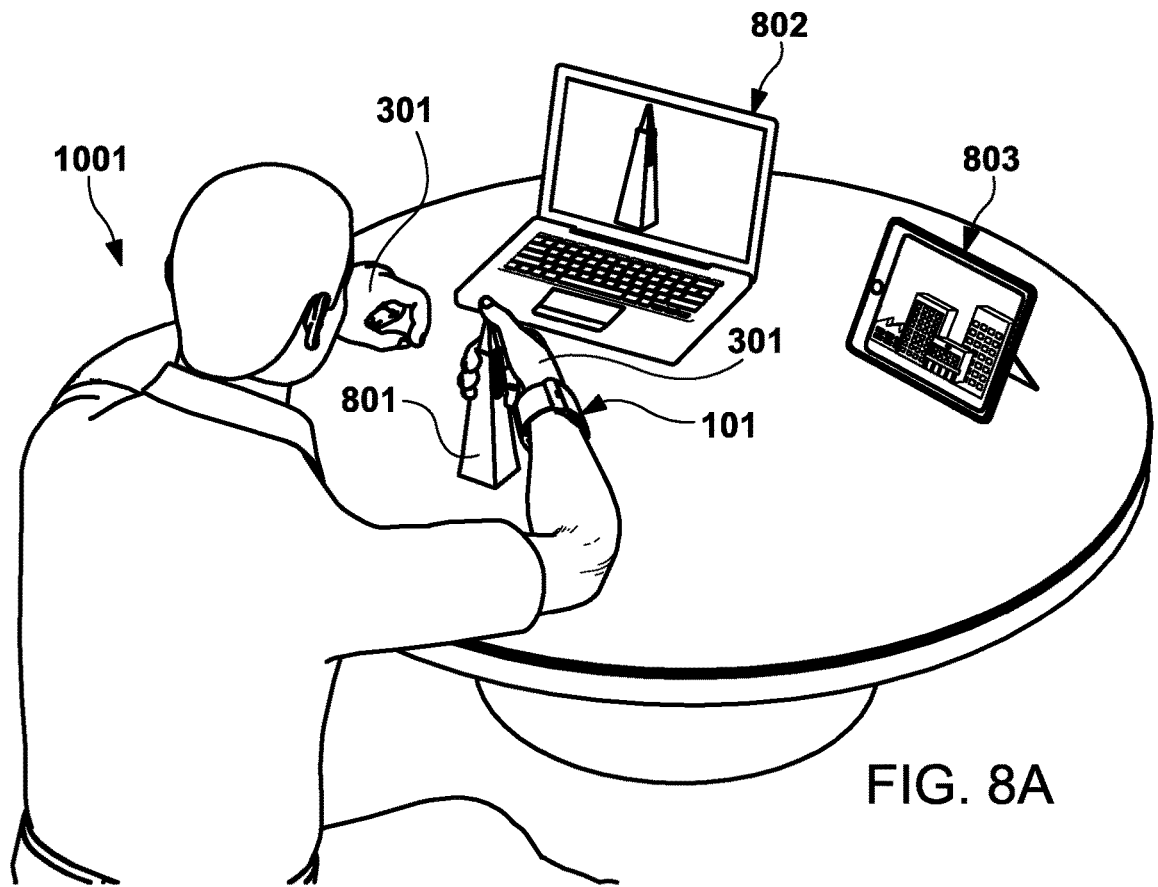
FIG. 8A is a perspective view illustrating the user interfacing with two networked devices and using a wrist console to map, image and model a scanned physical object into a virtual computing environment on an external networked device.

FIG. 8A is a perspective view illustrating the user interfacing with two networked devices and using the wrist console 101 to map, image and model a scanned physical object into a virtual computing environment on an external networked device 802.

Figure 8B:
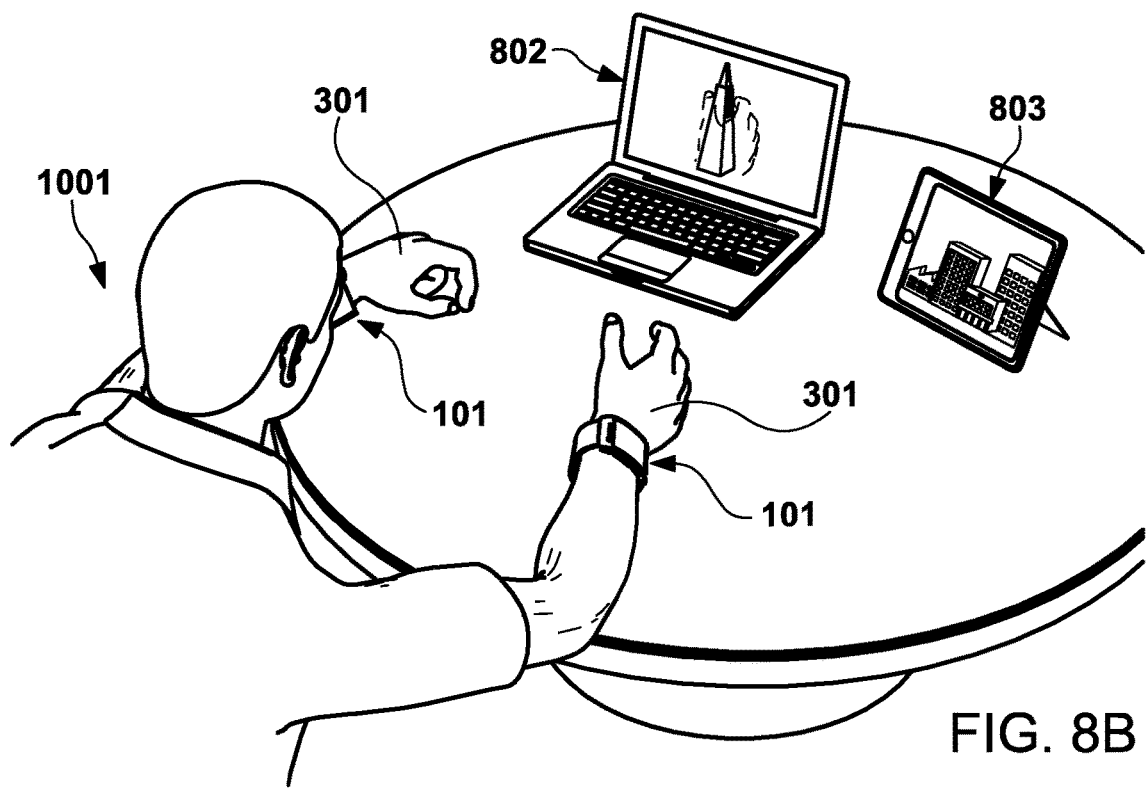
FIG. 8B is a perspective view illustrating the user operating a left and right wrist console as a two hand gesture interface controller to interface and manipulate a 3D computer model scanned and modeled by the wrist console and wirelessly uploaded to an external networked device.

FIG. 8B is a perspective view illustrating the user operating a left and right wrist console 101 as a two hand gesture interface controller to interface and manipulate a 3D computer model scanned and modeled by the wrist console 101 and wirelessly uploaded to an external networked device 802.

Figure 8C:
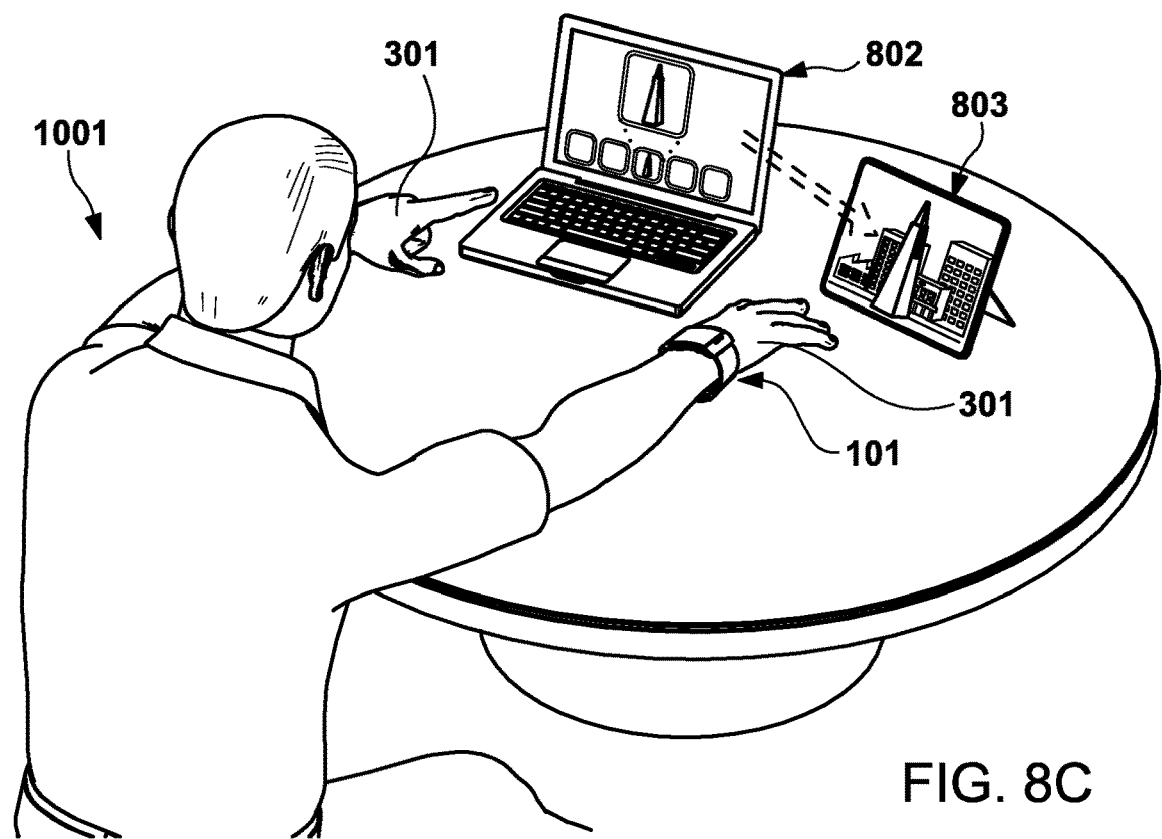
FIG. 8C is a perspective view illustrating the user selecting a file, document or program on one external networked device.

FIG. 8C is a perspective view illustrating the user selecting a file, document or program on one external networked device 802 and with a gesture, voice or other UI command wirelessly transferring the file, document or program to a second networked device 803 using the wrist console as a data bridge between two networked devices.

Figure 8D:
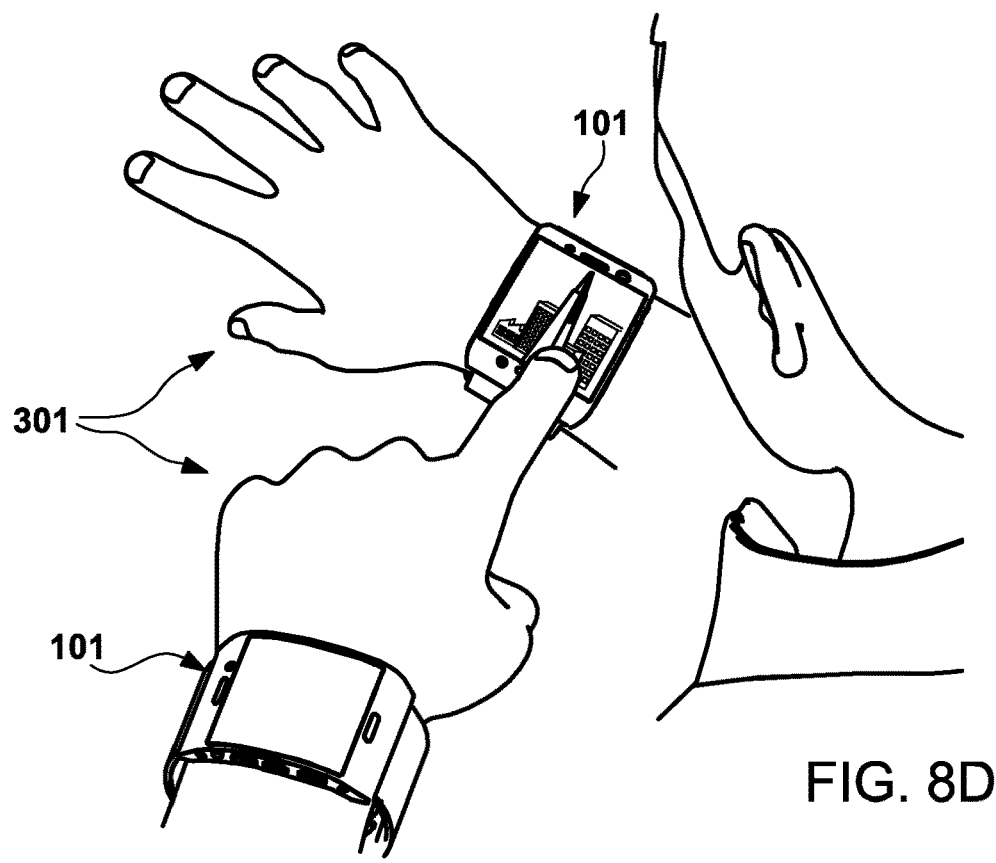
FIG. 8D is a perspective view illustrating the user operating and controlling a 3D scanned and modeled object on a wrist console touchscreen interface.

FIG. 8D is a perspective view illustrating the user operating and controlling a 3D scanned and modeled object on the wrist console 101 touchscreen interface.

Figure 9A:
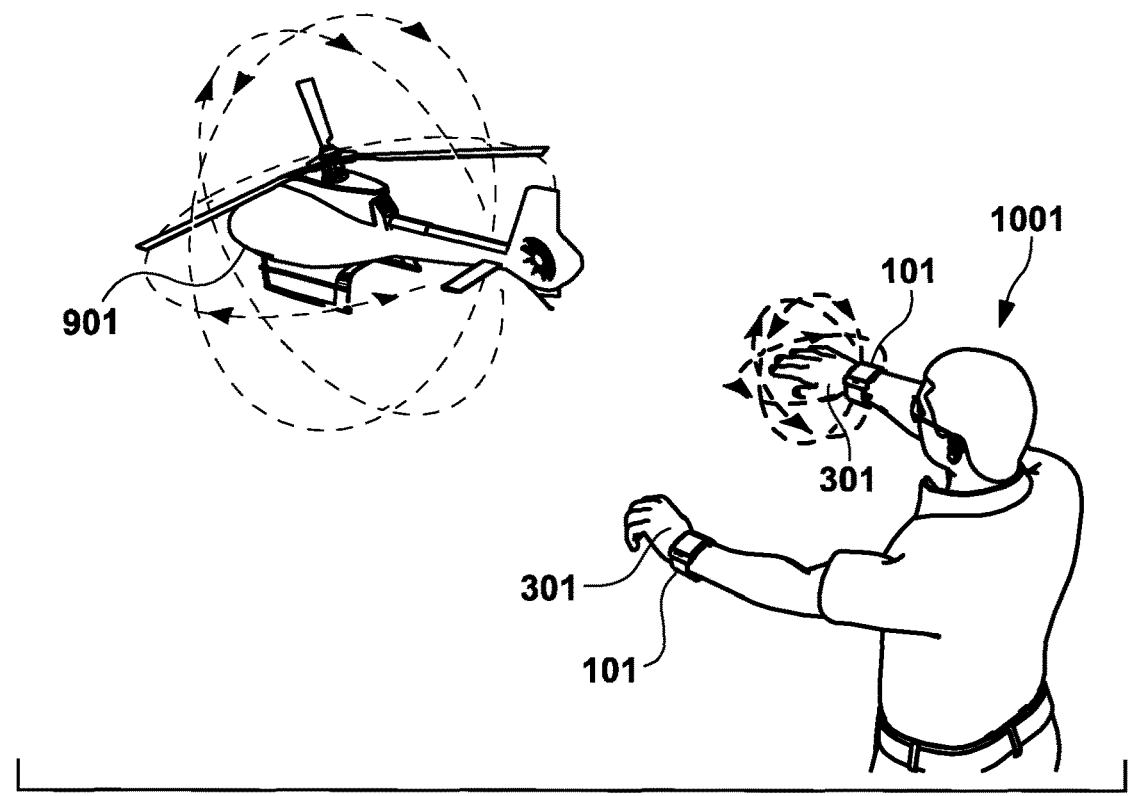
FIG. 9A is a perspective view illustrating a user wirelessly interfacing and controlling a remote device or vehicle.

FIG. 9A is a perspective view illustrating a user wirelessly interfacing and controlling a remote device or vehicle 901 using a wide or local area peer-to-peer wireless network or via the Internet using a wide or local area Internet connection.

Figure 9B:
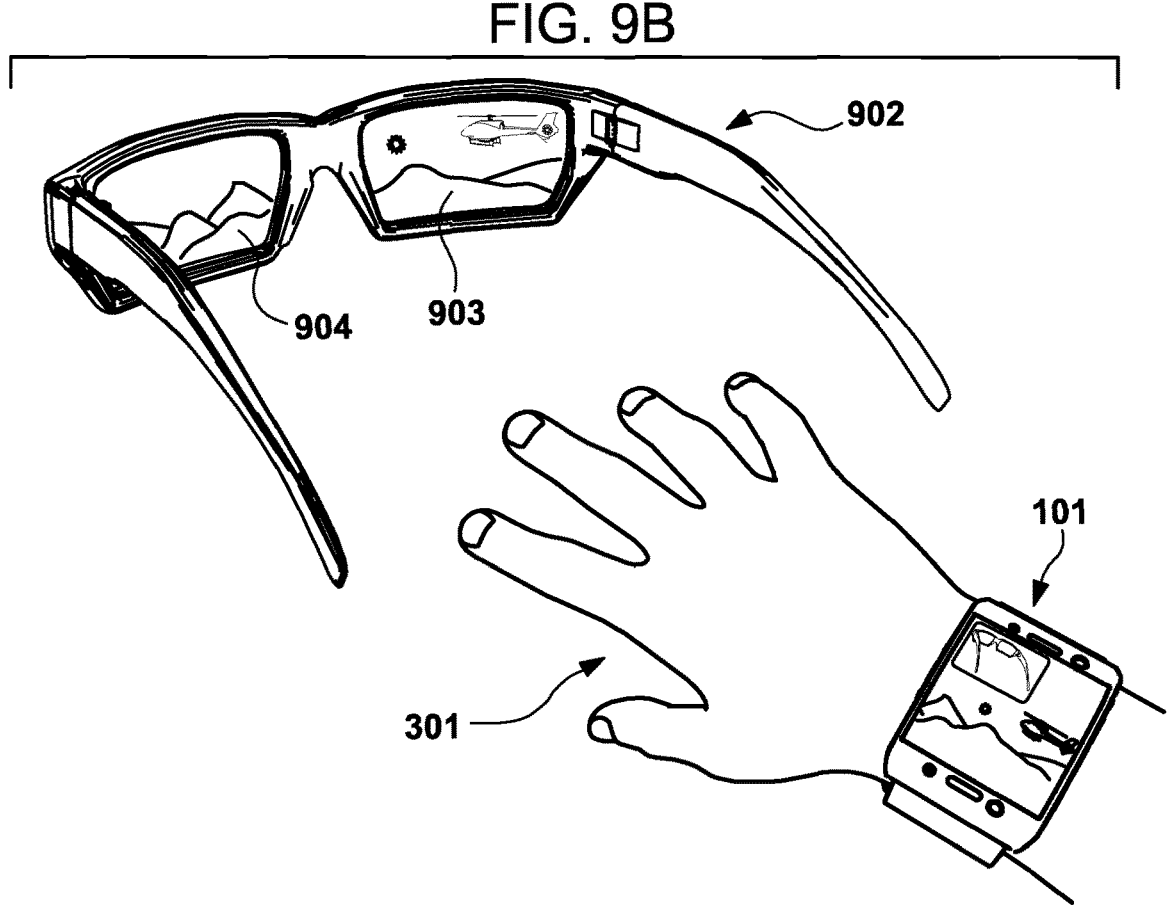
FIG. 9B is a perspective view illustrating a user wirelessly sending and receiving real-time voice, data, video and multimedia content to and from a remote device.

FIG. 9B is a perspective view illustrating a user wirelessly sending and receiving real-time voice, data, video and multimedia content to and from a remote device 901, streaming the data and multimedia content in 3D to a left 904, and right 903, binocular heads up display 902.

Figure 10A:
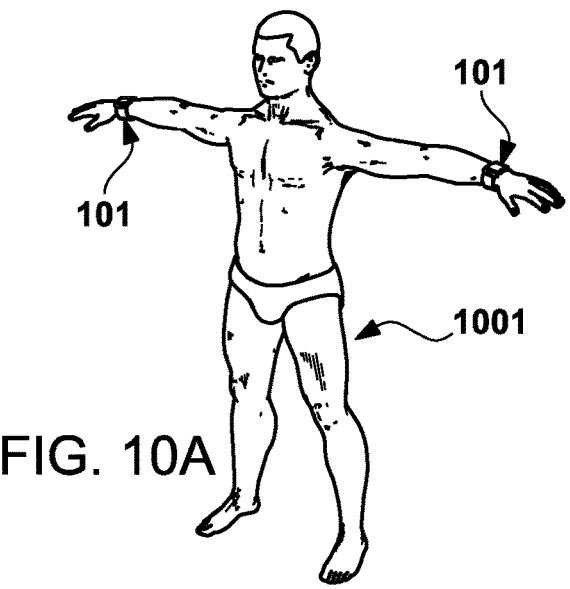
FIGS. 10A and 10B are perspective views illustrating a wrist console full body scanning, depth mapping and imaging process where a user performs a body scan and a 3D computer model of the user is generated.
Figure 10B:
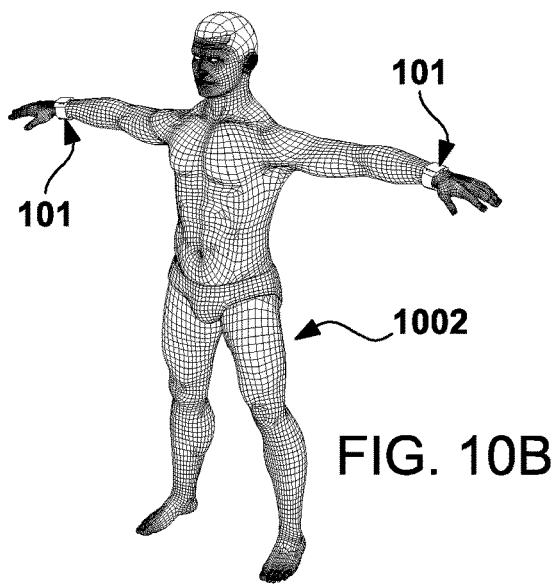

FIGS. 10A and 10B are perspective views illustrating the wrist console 101 full body scanning, depth mapping and imaging process where a user 1001 performs a body scan and a 3D computer model 1002 of the user is generated.

Figure 10C:
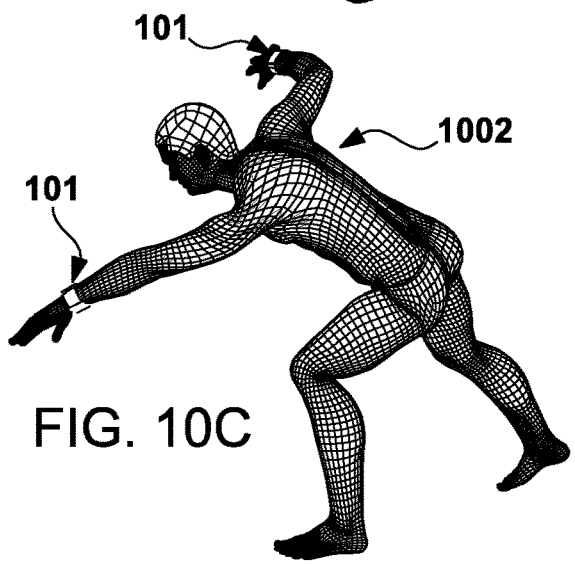
FIGS. 10C and 10D are perspective views illustrating the user in different positions and performing different body motions enabling the wrist console to map and image the body in multiple positions and analyze the flexibility and mobility of the user to more accurately generate the body rigging for the 3D computer model and replicate the users motions in a virtual computing environment.
Figure 10D:
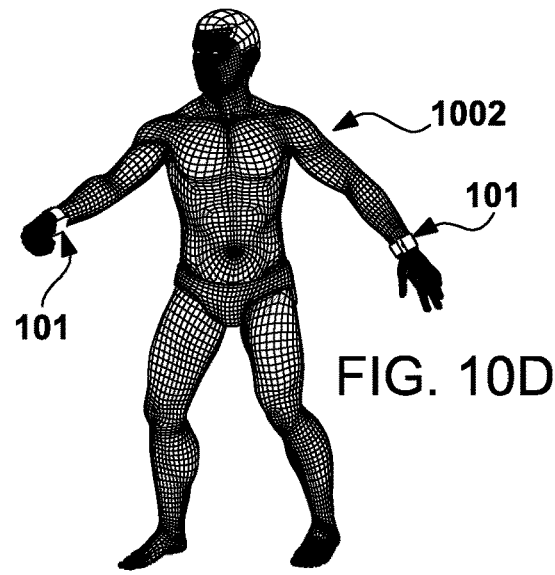

FIGS. 10C and 10D are perspective views illustrating the user in different positions and performing different body motions enabling the wrist console 101 to map and image the body 1002 in multiple positions and analyze the flexibility and mobility of the user to more accurately generate the body rigging for the 3D computer model and replicate the users motions in a virtual computing environment.

Figure 10E:
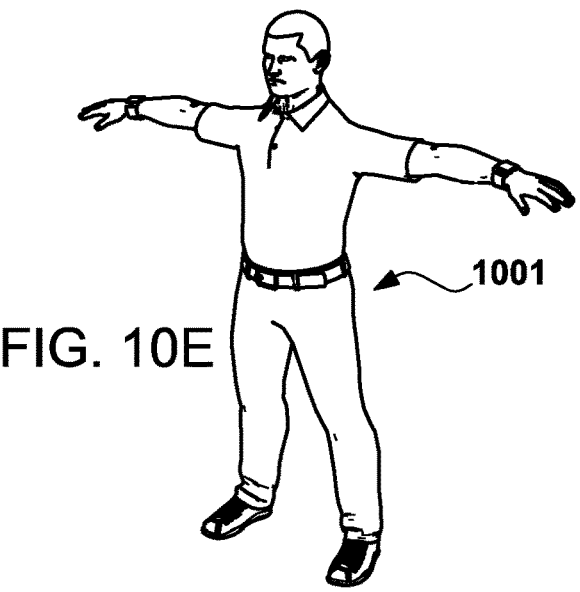
FIGS. 10E and 10F are perspective views illustrating the 3D mapping and imaging of the user and a 3D computer model with clothing.
Figure 10F:
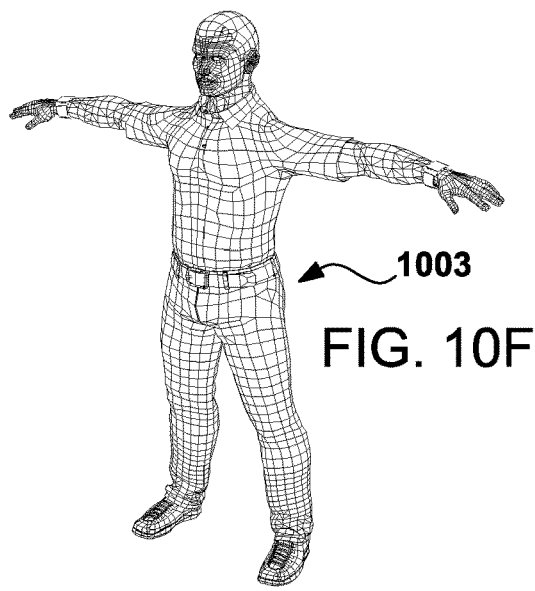

FIGS. 10E and 10F are perspective views illustrating the 3D mapping and imaging of the user 1001 and the 3D computer model 1003 with clothing. This may be accomplished by light mapping and 3D imaging the user's 1001 physical clothing or by mapping virtual clothing onto the 3D model 1003 in a computing environment.

Figure 11A:
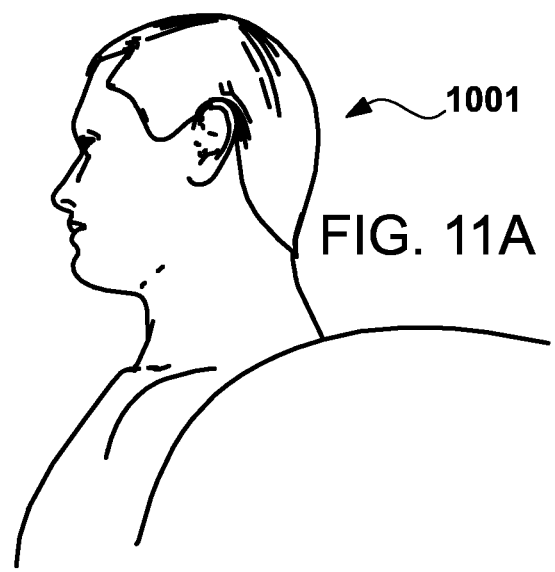
FIGS. 11A and 11B are perspective views depicting the camera view from a top module of a wrist console.
Figure 11B:
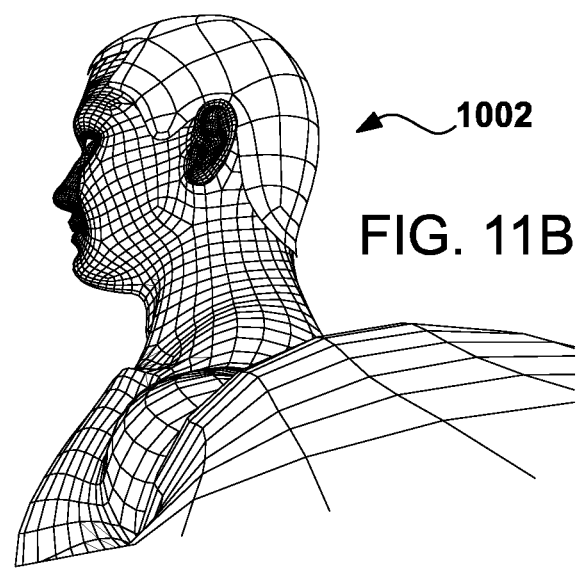
Figure 11C:
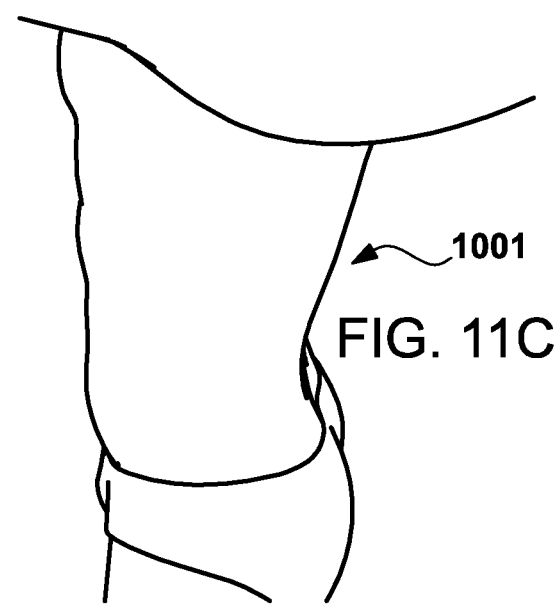
FIGS. 11C and 11D are perspective views depicting the camera view from a bottom module of a wrist console.
Figure 11D:
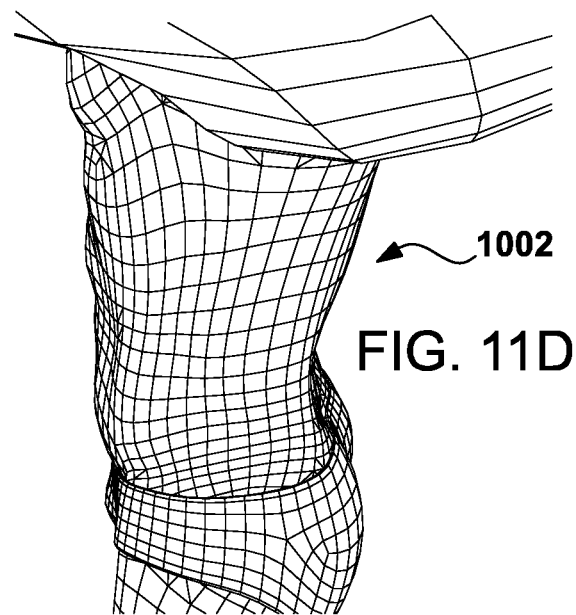

FIGS. 11A-11D are perspective views illustrating the body mapping and imaging process from the perspective of each of the wrist console's 101 body facing cameras 108 with FIGS. 11A and 11B depicting the camera view from the top module and FIGS. 11C and 11D depicting the camera view from the bottom module 103. The wrist console 101 is not shown in FIGS. 11A-11D because the figures depict the perspective of the cameras.

Figure 12A:
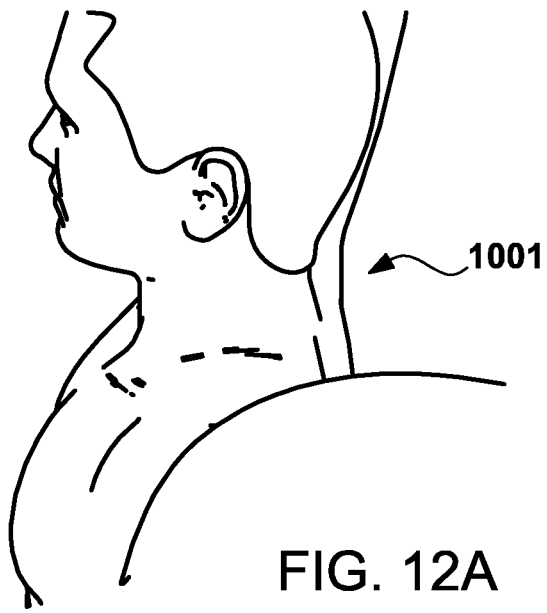
FIGS. 12A and 12B are perspective views depicting the camera view from a top module of a wrist console.
Figure 12B:
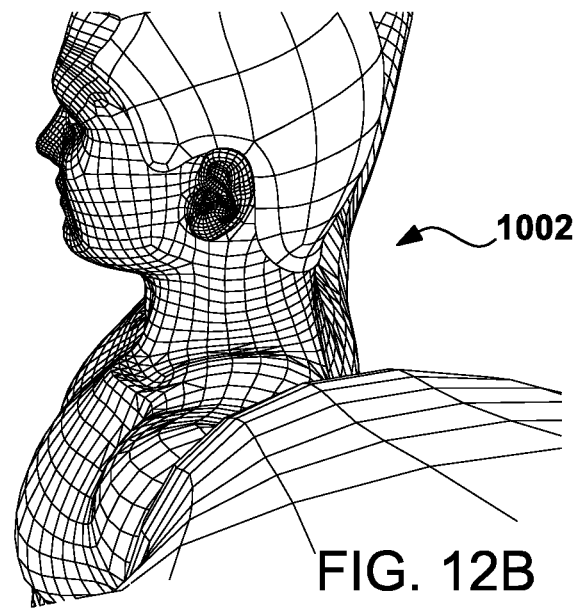
Figure 12C:
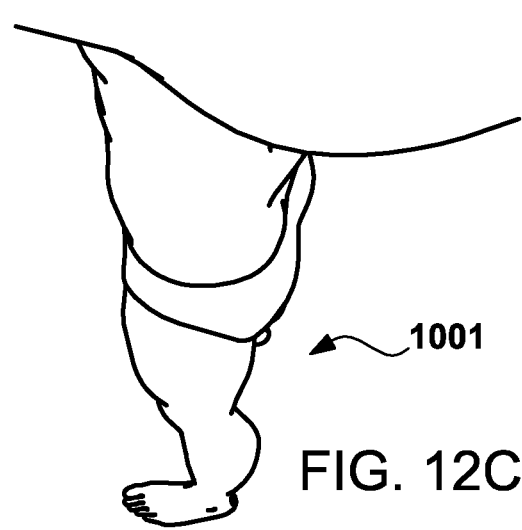
FIGS. 12C and 12D are perspective views depicting the camera view from a bottom module of a wrist console.
Figure 12D:
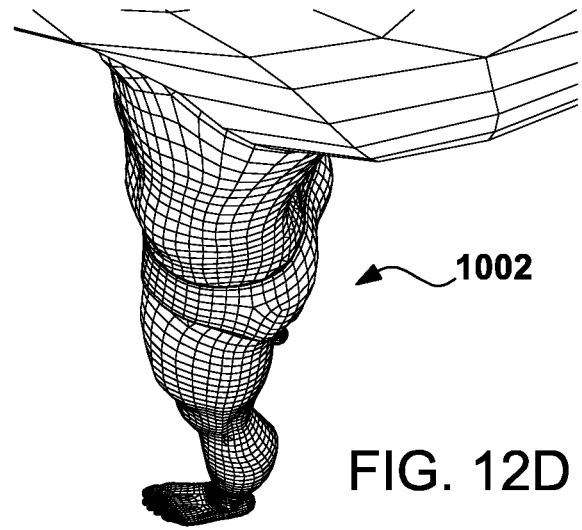

FIGS. 12A-12D are perspective views illustrating the body mapping and imaging process from the perspective of each of the wrist consoles 101 body facing cameras 108 with FIGS. 12A and 12B depicting the camera view from the top module 102 and FIGS. 12C and 12D depicting the camera view from the bottom module 103. In FIGS. 12A-12D the users arms and hands are stretched out higher over the users head enabling the cameras to scan a different portion of the users body.

Figure 13A:
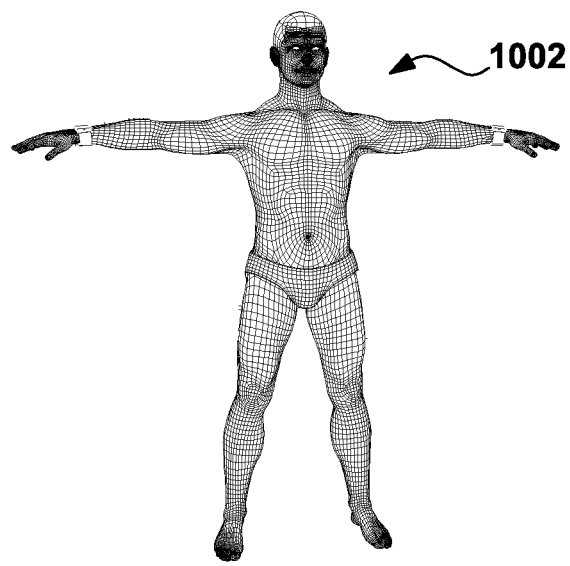
FIGS. 13A-13C are perspective views illustrating the body rigging process.
Figure 13B:
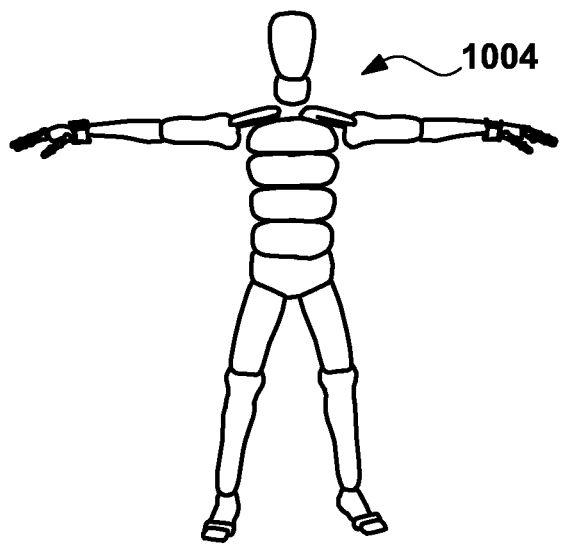
Figure 13C:
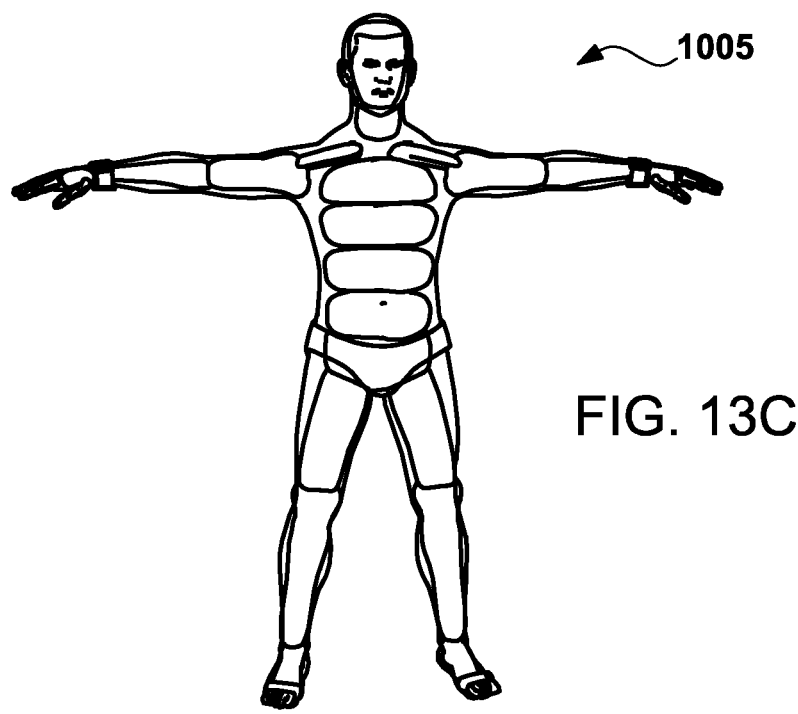

FIGS. 13A-13C are perspective views illustrating the body rigging process with FIG. 13A illustrates the surface mesh of depth and color mapped model of the user 1002. FIG. 13B illustrates a full body character rigging (rig) that is conformed to the precise dimensions and characteristics of the mapped computer model of the user 1002. And FIG. 13C illustrates the incorporation of the character rig.

Figure 14A:
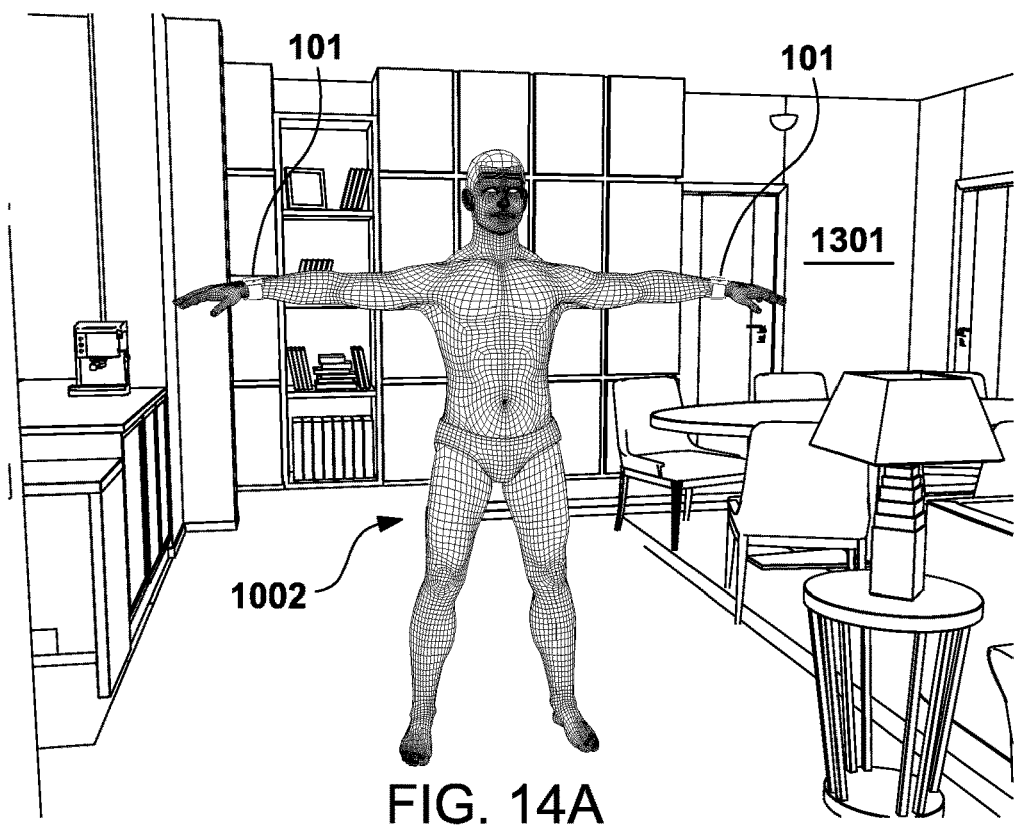
FIGS. 14A and 14B are perspective views illustrating the users 3D computer model spatial position and location in a mapped physical environment.
Figure 14B:
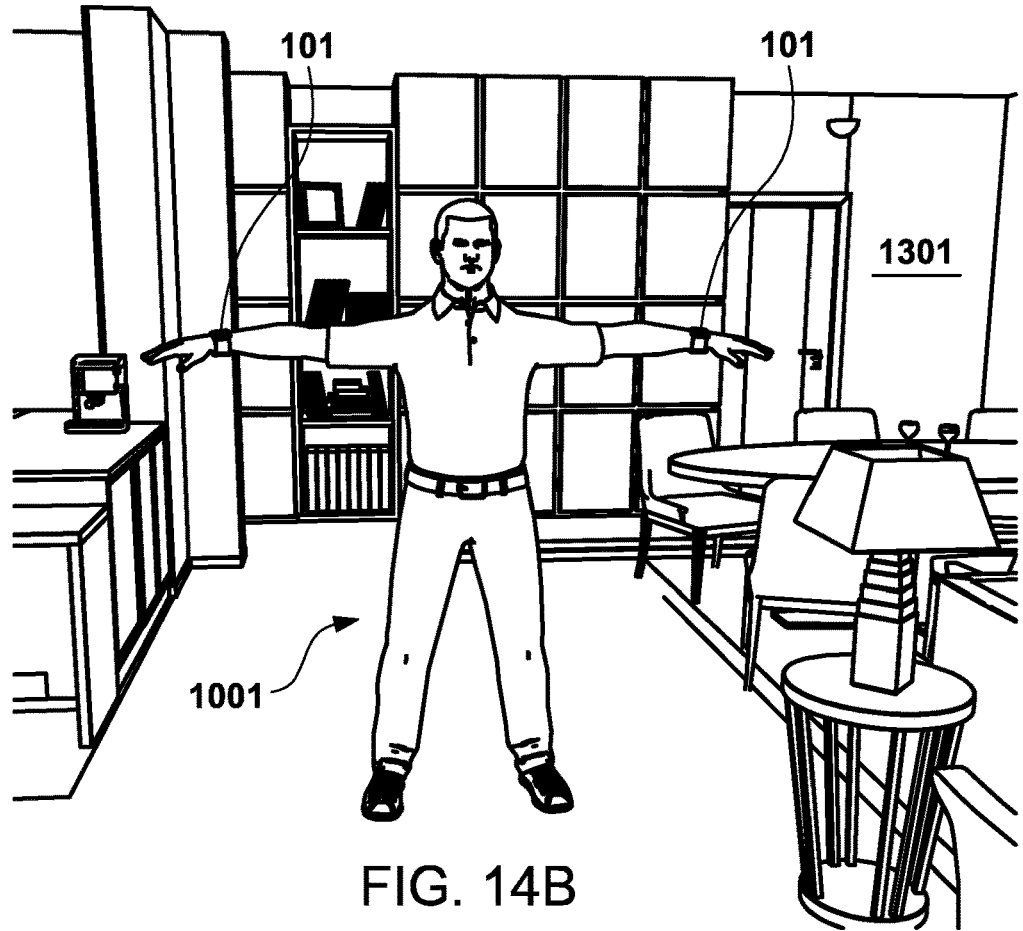

FIGS. 14A and 14B are perspective views illustrating the user's 1001 and the users 3D computer model 1002 spatial position and location in a mapped physical environment 1301 identified and mapped during the 3D body mapping and imaging process.

Figure 15:
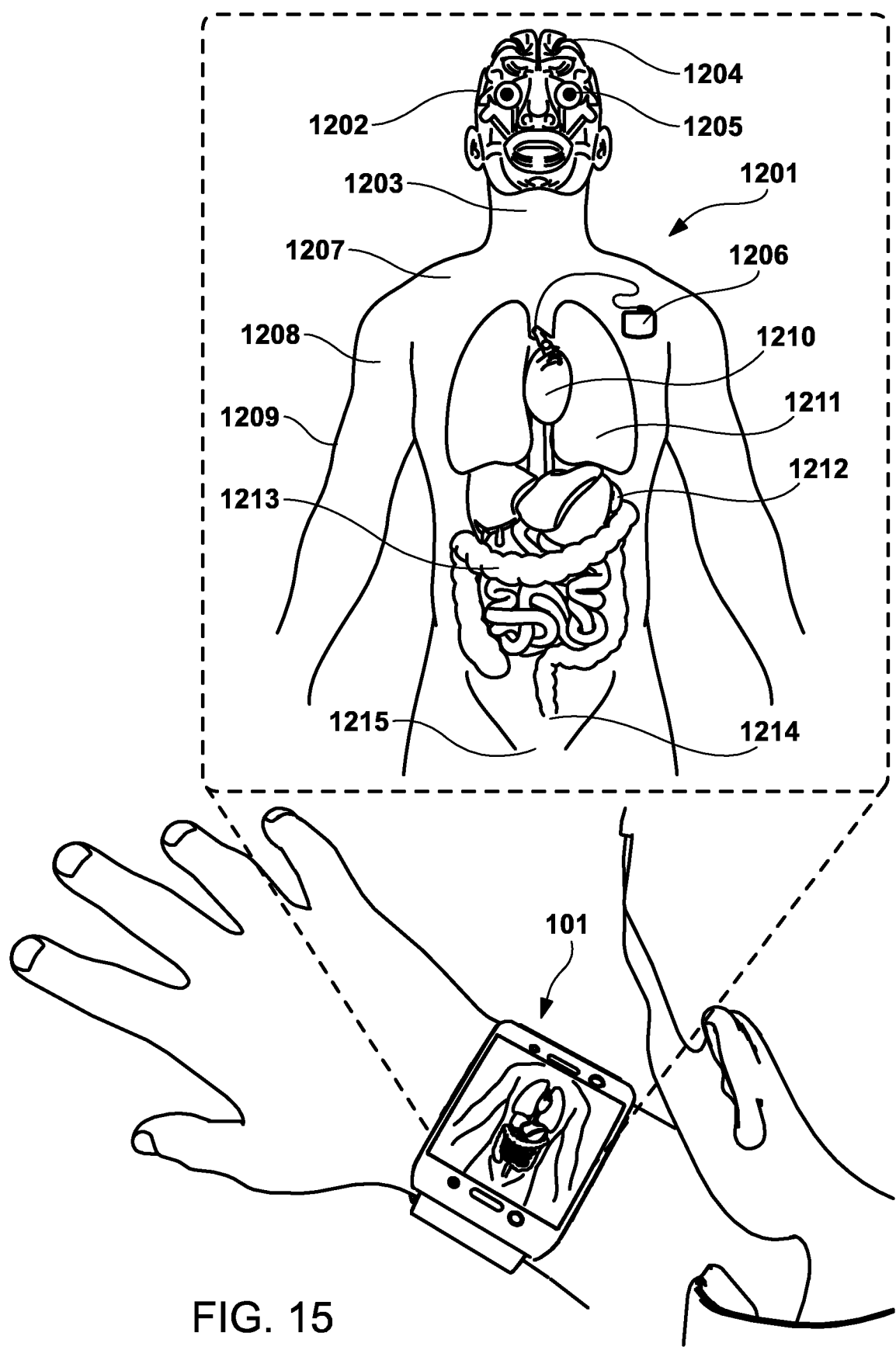
FIG. 15 is a perspective view illustrating a virtual internal body map of a user's anatomy and networked, sensors, implanted devices and prosthetics

FIG. 15 is a perspective view illustrating a virtual internal body map 1201 of the users anatomy and all networked, sensors, implanted devices and prosthetics all mapped and wirelessly controlled by the wrist console 101. In FIG. 15 the wrist console 101 using onboard, external, implanted or ingested networked body sensors to map each of the users body systems; Nervous System 1202, Endocrine System 1203, Skeletal System 1207, Muscular System 1208, Integumentary System 1209, Cardiovascular System 1210, Respiratory System 1211, Lymphatic System 1212, Digestive System 1213, Urinary System 1214 and Reproductive System 1215. The wrist console 101 also networks and interfaces with all internal data and multimedia interfacing systems, depicted in FIG. 15 as a Brain Machine Interface (BMI) 1204, Prosthetics depicted in FIG. 15 as a prosthetic eye 1205, and other implanted devices depicted in FIG. 15 as a pacemaker 1206.

Figure 16A:
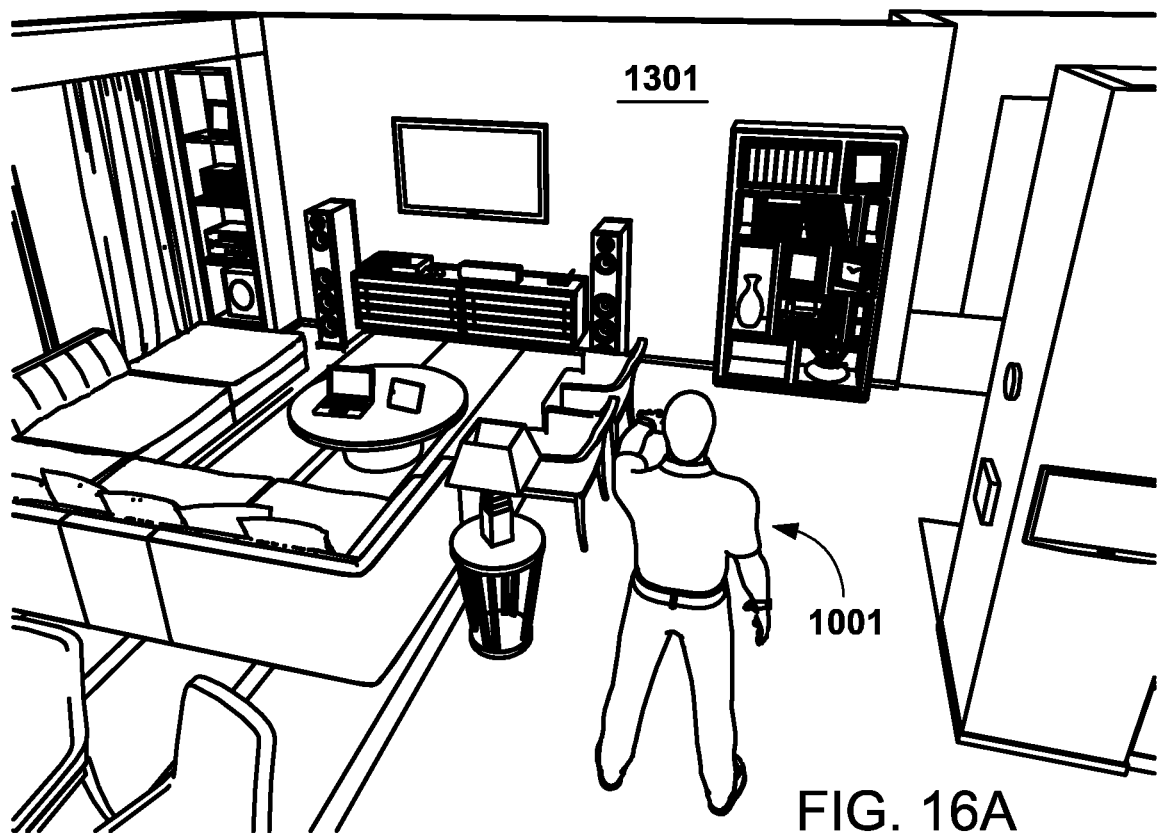
FIGS. 16A and 16B are perspective views illustrating a wrist console space, object and environment 3D light and image mapping process.
Figure 16B:
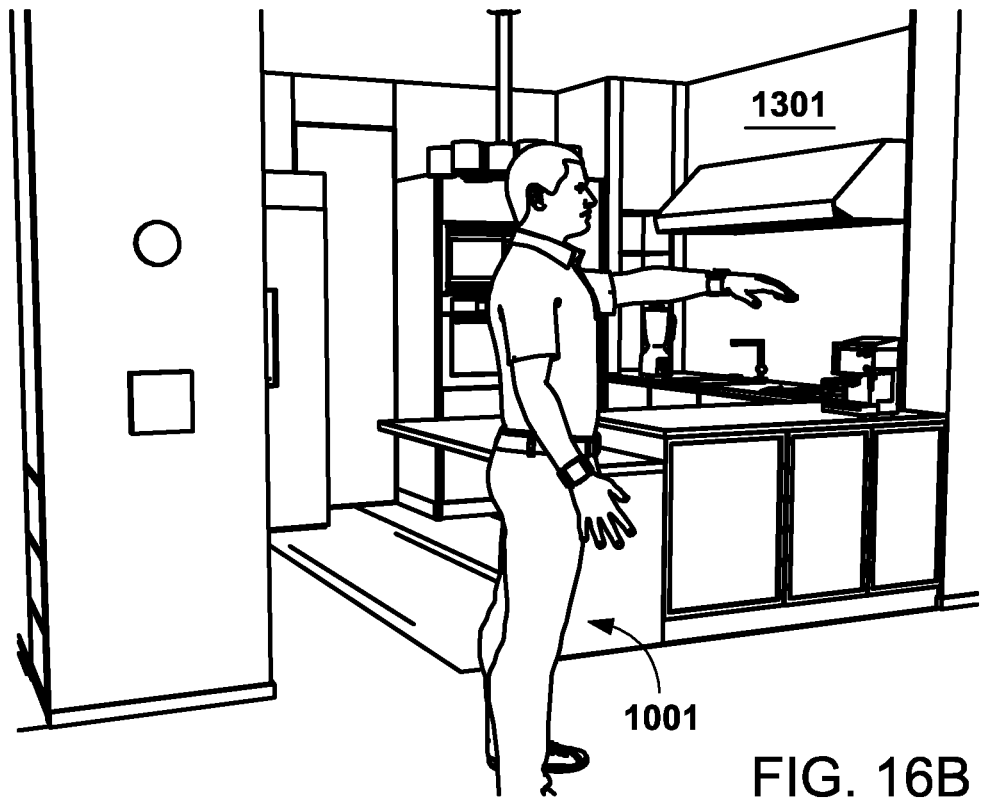

FIGS. 16A and 16B are perspective views illustrating the wrist console 101 space, object and environment 3D light and image mapping process shown in FIGS. 16A and 16B as a residential living space 1301. FIG. 16A depicts the user 1001 3D mapping and imaging the living and dining section 1306 while FIG. 16B depicts the user 1001 mapping the kitchen section 1304 of the residential living space 1301.

Figure 17A:
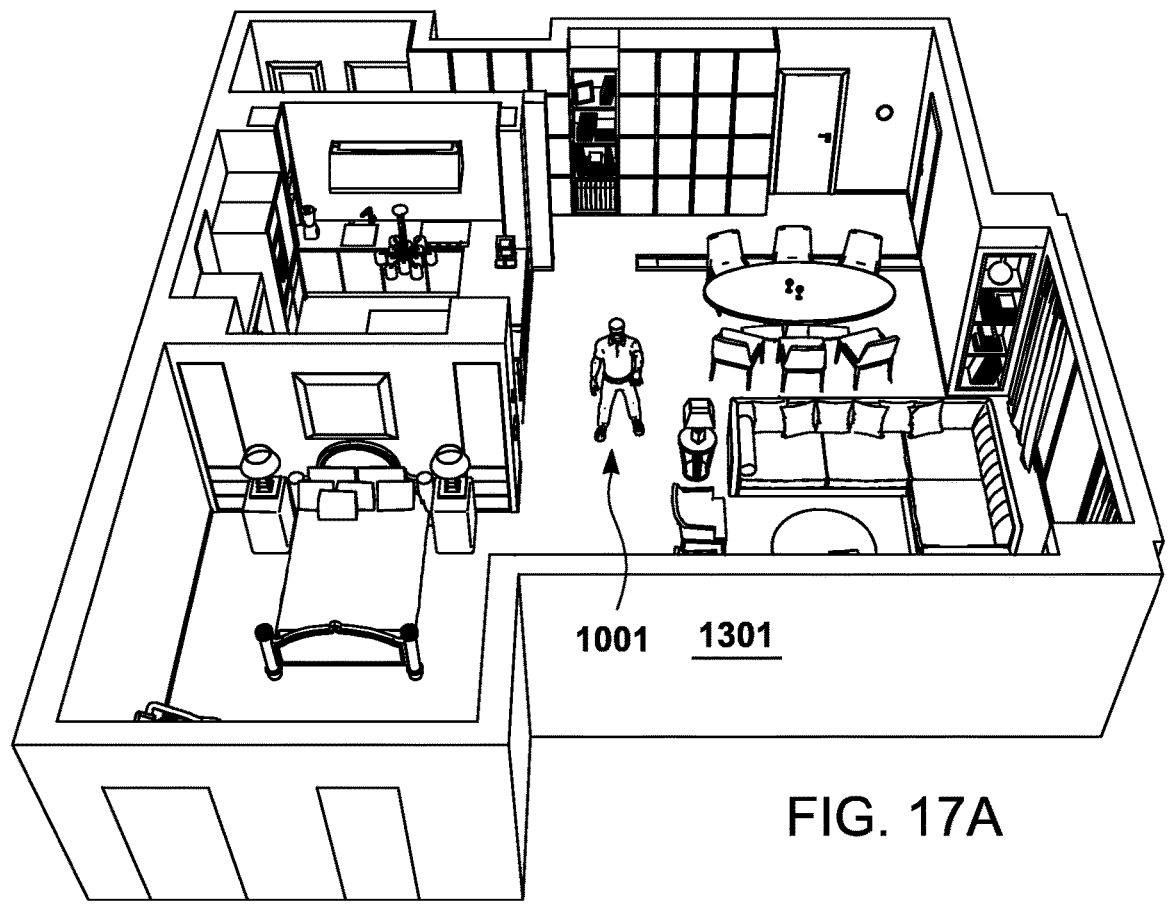
FIGS. 17A and 17B are perspective views of the user standing in a residential living space.
Figure 17B:
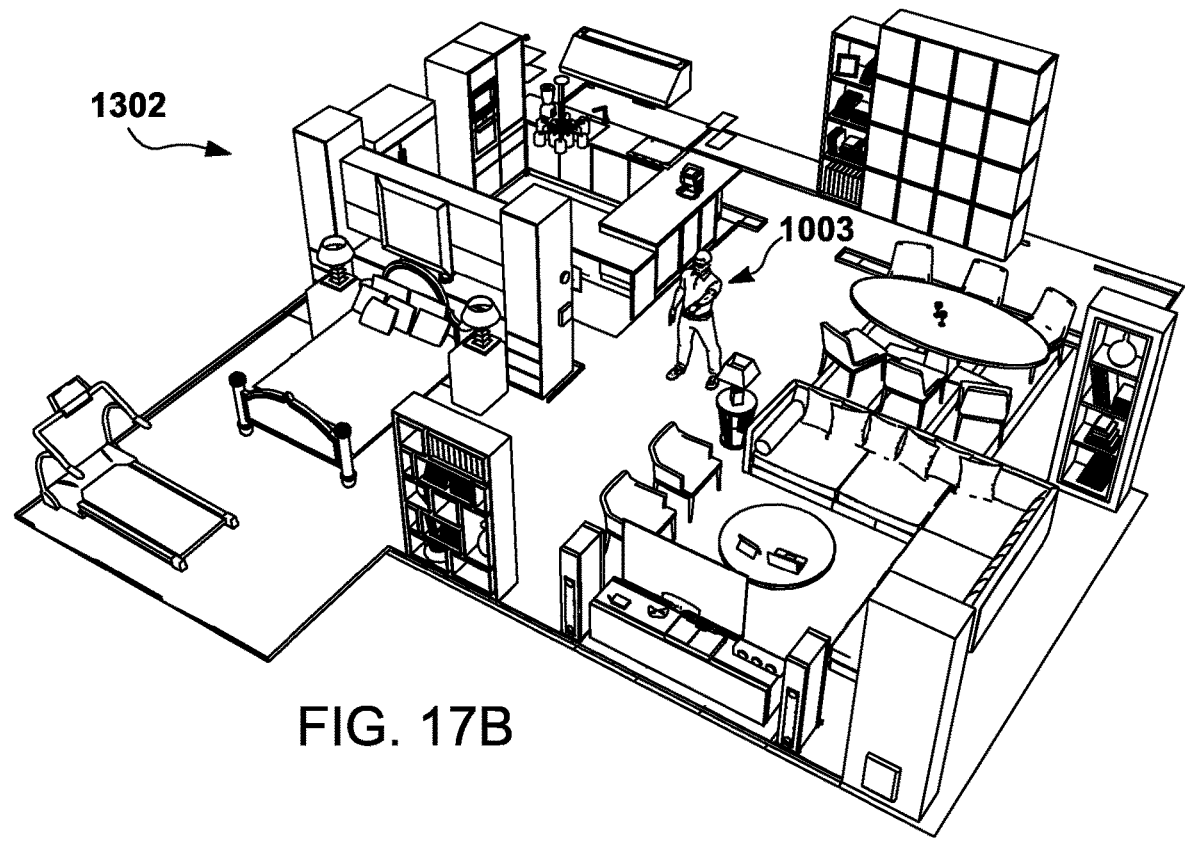

FIGS. 17A and 17B are perspective views of the user standing in a residential living space 1301. FIG. 17A illustrates the user standing in the physical residential living space 1301 providing an example of a potential 3D mapped environment. FIG. 17B illustrates an overhead perspective view of a 3D mapped user 1003 and environment 1302 with all mapped people, objects, devices and environments stored securely on the wrist console or uploaded wirelessly to a user authorized account on the Internet or other network or database.

Figure 18:
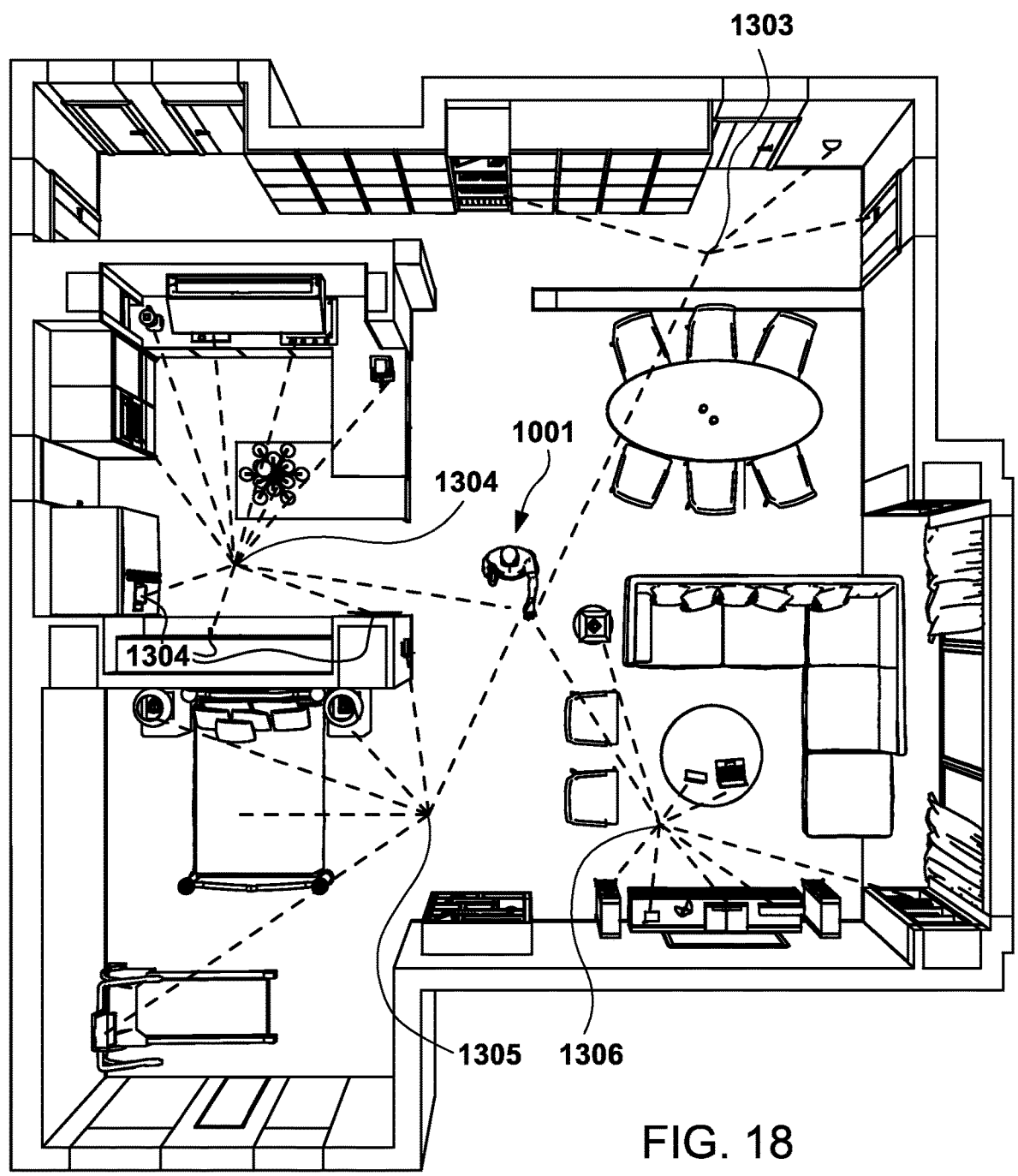
FIG. 18 is an overhead perspective view of the user and a wrist console identifying and mapping the location, device type, functions and applications, data, power and other system specifications and available networks and interfacing options for all networked devices in the in the residential living space.

FIG. 18 is an overhead perspective view of the user 1001 and the wrist console 101 identifying and mapping the location, device type, functions and applications, data, power and other system specifications and available networks and interfacing options for all networked devices in the in the residential living space 1301.

FIGS. 19A and 19B are perspective views of a professional tennis player 1401, wearing the wrist console 101, playing tennis on a real outdoor tennis court 1404 while the user 1001 is testing his skills at home by attempting to return the tennis ball 1403 hit by the tennis player in real-time in a virtual gaming environment on the users 1001 television or other display 1405.

Figure 20A:
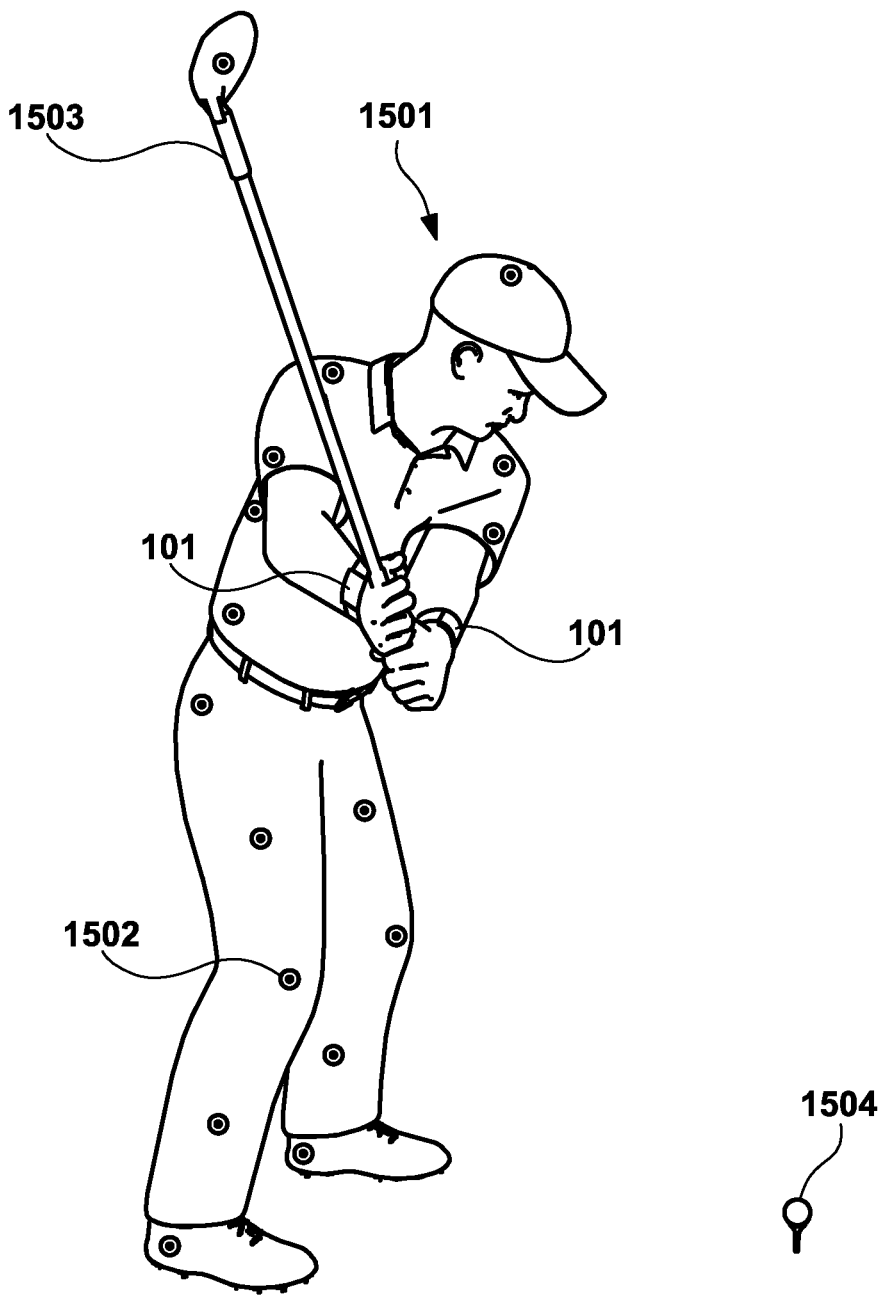
FIGS. 20A, 20B, and 20C are perspective views of a professional golfer mapping his swing, the ball, and virtualizing the player's entire game of golf in real time.
Figure 20B:
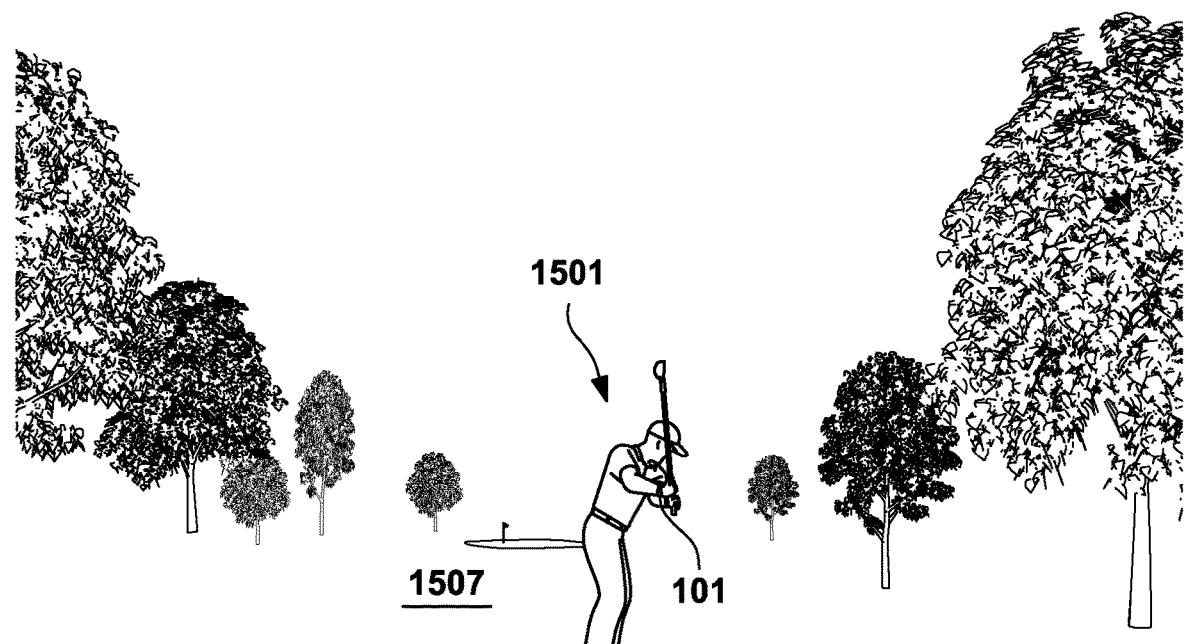
Figure 20C:
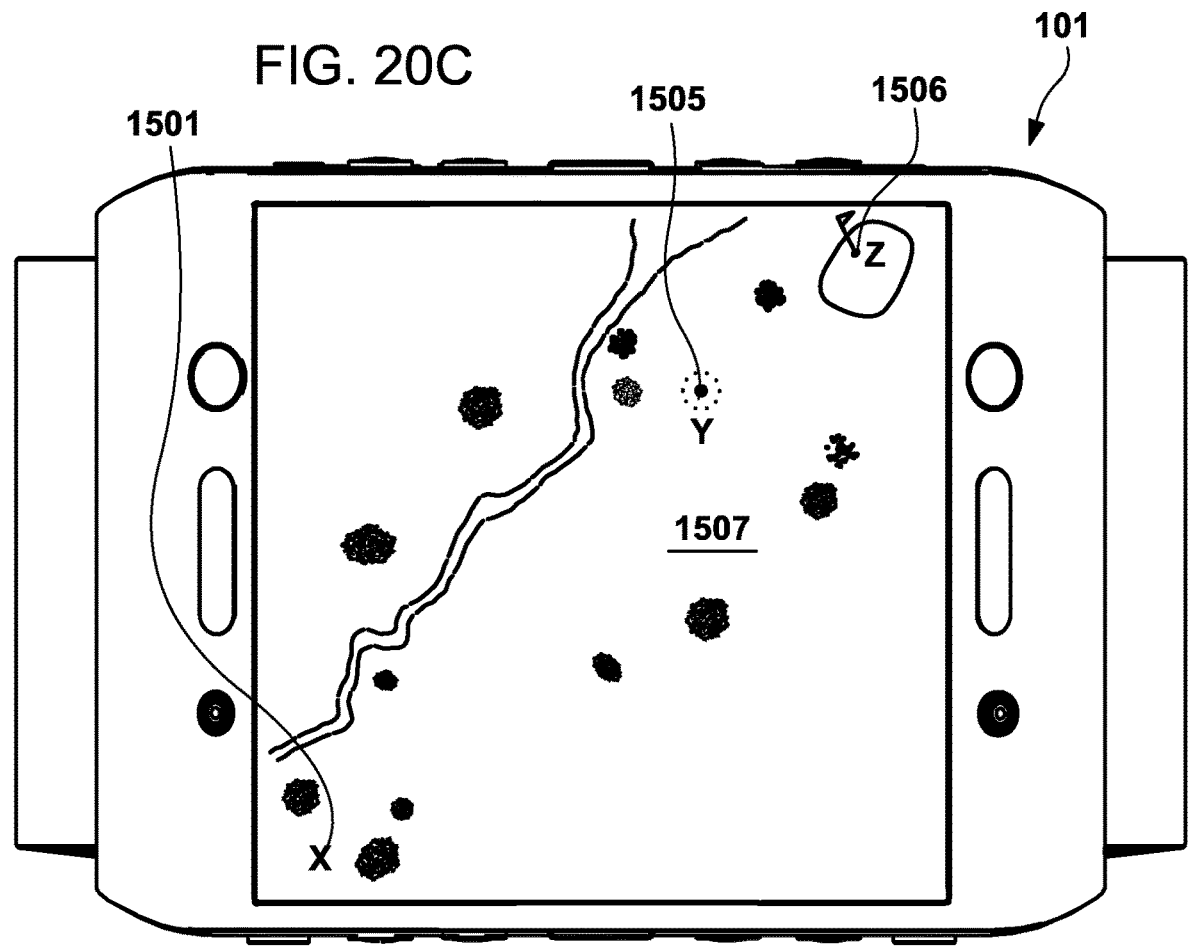

FIGS. 20A-20C are perspective views of a professional golfer 1501 mapping his swing, the ball 1504, and virtualizing the players entire game of golf in real time. FIG. 20A is a perspective view illustrating a professional golfer swinging at a golf ball 1504. The golfer has sensors on or embedded in his clothing and shoes 1502 and equipment 1503 enabling the wrist console 101 to map every detail of the golfers body motion during the swing.

Figure 21:
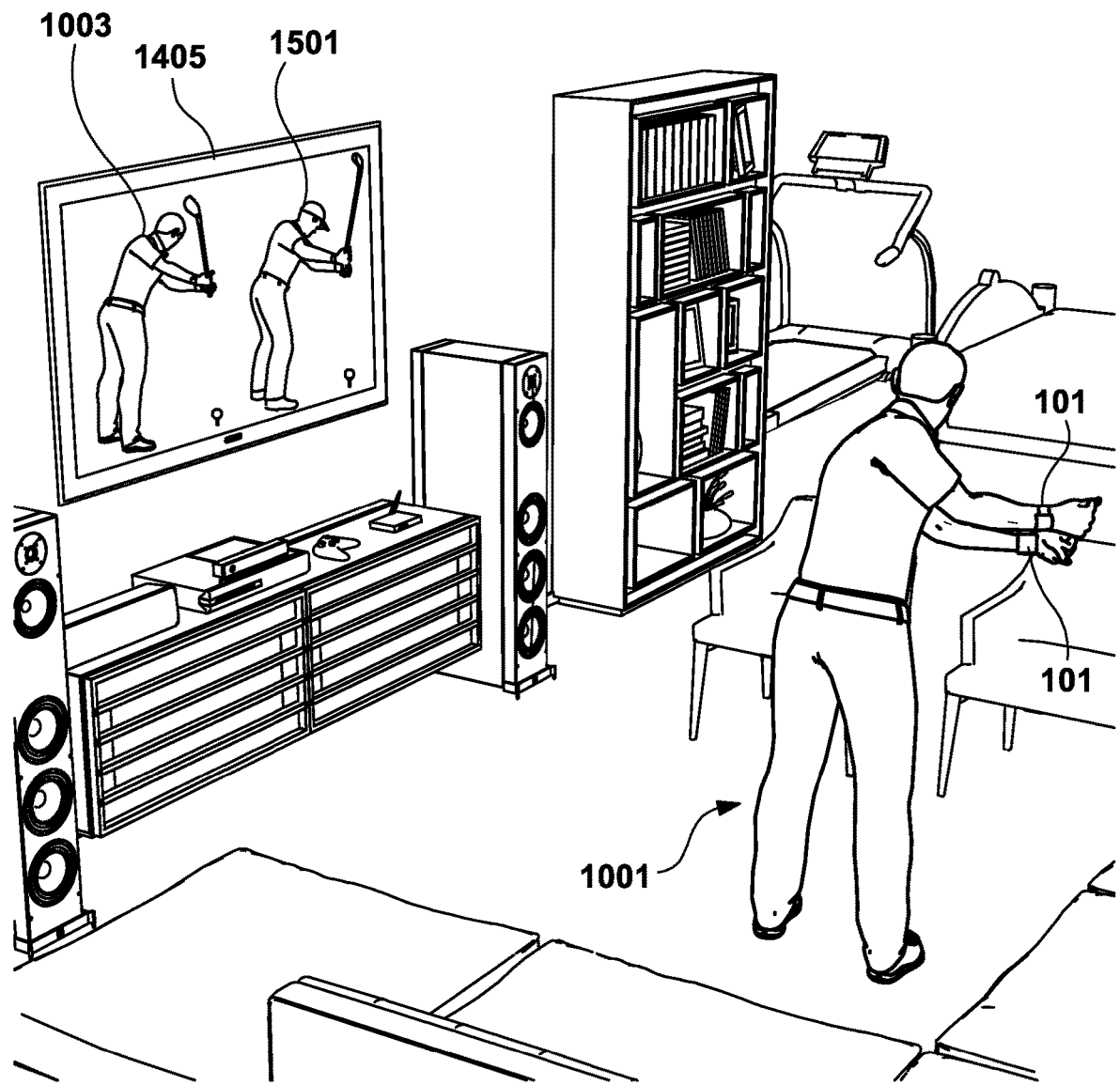
FIG. 21 is a perspective view illustrating a professional golfer on a golf course.

FIG. 21 is a perspective view illustrating the professional golfer 1501 on the golf course mapping his swing and remotely mapping and monitoring the height, speed, trajectory, landing and resting position of a sensor enabled networked golf ball on the wrist console 101.

Figure 22:
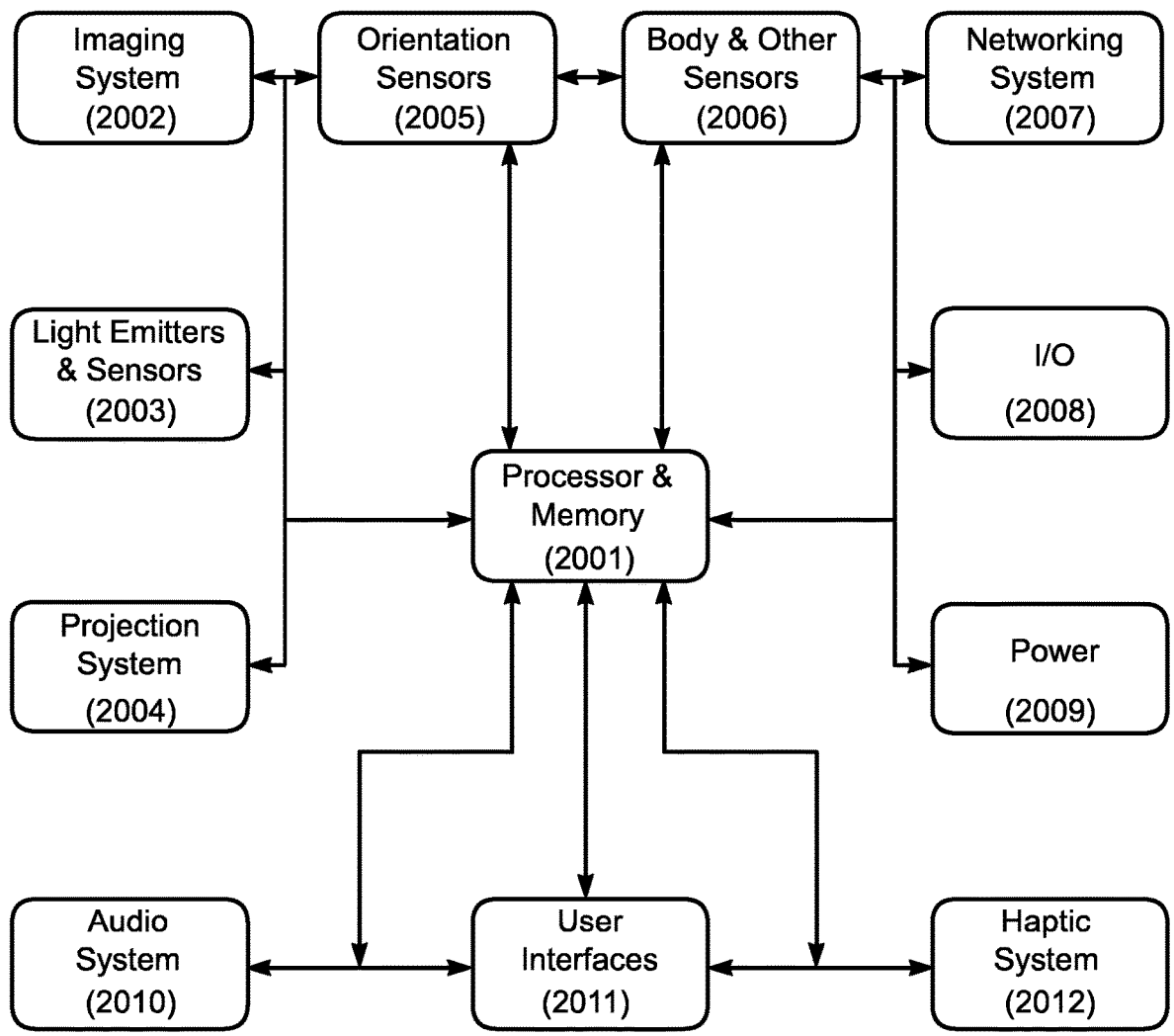
FIG. 22 is a schematic diagram of a wrist console.

FIG. 22 is a schematic diagram of the connections of various components envisioned to be part of a wrist console device.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

The invention claimed is:

1. An apparatus that is wearable by a user, comprising:
a housing module housing a processor, light emitters and optical sensors, wherein the processor is configure to communicate with said light emitters and said optical sensors;
one or more projectors;
and
an imaging system having a field of view;
wherein the processor is configured to:
communicate with the imaging system,
dynamically image and map one or more surfaces of any of:
at least a portion of the user's body,
an object held by the user,
an object near the user, or
at least a portion of an environment surrounding the user;
wherein the apparatus is configured to:
acquire the spatial position, direction motion, and orientation of the apparatus by any one or combination of onboard accelerometers, altimeters, compasses and gyroscopes, as well as GPS and radio frequency direction signal and location data to continuously identify the relation position of the apparatus, imaging system, light emitters and sensors to reflected and imaged surfaces to assign that data to each light point and color pixel in the scanned surfaces;
dynamically map the spatial position of the scanned surfaces and the relational position of the projector to the scanned surface based on the acquired spatial position, direction motion, and orientation of the apparatus to dynamically determine the relational position of the imaging system to the dynamically imaged and mapped surfaces;
and
dynamically project any of an undistorted image, an undistorted graphic user interface, or any combination thereof on the imaged and mapped surfaces, with the projectors, based on the dynamically determined relational position of the imaging system to the dynamically imaged and mapped surfaces.

2. The apparatus of claim 1, wherein the imagining system includes one or more light emitters and one or more optical sensors, and wherein the optical sensors include a camera.

3. The apparatus of claim 2, wherein the camera is configured to scan any of objects and surfaces within close proximity of the user; and
wherein the processor is configured to process data received from the camera to create a map of the scanned objects or surfaces.

4. The apparatus of claim 3, wherein the camera is configured to scan any of objects and surfaces within close proximity of the user, and the processor is configured to determine any of distance and relational position between the scanned objects or surfaces and the apparatus.

5. The apparatus of claim 4, wherein the scanned multiple objects and surfaces within close proximity to the user include any of:
clothing associated with the user;
a device worn by the user;
a device held by the user; or
a device, object or surface associated with the environment surrounding the user.

6. The apparatus of claim 4, further comprising:
a motion and orientation determination module configured to determine any of the directional motion, speed, spatial position and orientation of the apparatus;

wherein the processor is configured to process data received from the motion and orientation determination module in connection with data received from the camera to identify the spatial and relational position of the apparatus to surrounding objects and surfaces.

7. The apparatus of claim 1, further comprising:
a sensing module configured to determine any of a health or fitness parameter of the user.

8. The apparatus of claim 7, wherein the health or fitness parameter includes any of:
heart rate,
heart electrical activity,
brain electrical activity,
muscle electrical activity,
galvanic skin response,
blood oxygen content,
blood glucose level,
body temperature,
body motion, or
body movement.

9. The apparatus of claim 1, wherein the processor is configured to:
receive gestural input of an interaction by the user with the projected image or graphic user interface on the scanned surfaces, utilizing at least one component of the imaging system; and
determine a user's interaction with the projected graphic user interface.

10. The apparatus of claim 9, wherein at least one of the projectors is configured to display any of an image, video, or multimedia content on one or more of the scanned surfaces, wherein the user can control or interface with the image, video, multimedia content, or graphic user interface.

11. The apparatus of claim 10, further comprising:
wherein two or more of the projectors are configured to operate independently or collectively to project one or more graphic user interfaces onto one or more surfaces and enable a user to interface and control one or more graphic user interfaces with another graphic user interface using one or more interfacing devices.

12. The apparatus of claim 1, further comprising:
an interfacing module including one or more interfacing systems to control the apparatus, a projected graphic user interface or another device, object, surface or interface.

13. The apparatus of claim 12, wherein one or more of the interfacing systems are assignable by the user for control of one or more tasks, functions, devices or applications.

14. The apparatus of claim 12, further comprising:
a touch and gesture interfacing system that is configured to:
determine a touch by the user on any of a physical or virtual device, object, surface or interface;
determine a gesture performed by the user based on the determined touch; and
transmit a signal to an external device based on the determined gesture.

15. The apparatus of claim 12, further comprising:
a microphone configured to capture audio and voice input commands from the user.

16. The apparatus of claim 12, further comprising:
a haptic interfacing module that is configured to:
sense any of finger, hand, wrist, and body movement of the user; and
produce a tactile feedback for the user, using the sensed movement.

17. The apparatus of claim 16, wherein the sensed movement is used for any of:
providing touch and gesture commands for any of a touch screen, a device control, a projection interface, and other user interface applications;
providing tactile response and more realism for any of object or application selection and control in a physical or virtual 2D or 3D environment;
interfacing with an interface that is projected on a surface;
interfacing with a virtual or physical interface that is assigned to or incorporated with any of a device, an object, or a surface;
indicating any of a locational, spatial or relational distance to any of a recognized object, person or an assigned contextual application; or
indicating any of an incoming call, an outgoing call, a text alarm, a health status, or other event or application.

18. The apparatus of claim 12, further comprising:
a plug-in interfacing module configured for adding additional interfacing systems to the interfacing module.

19. The apparatus of claim 1, further comprising:
a wireless networking and communications module configured for any of wireless voice, data, video and multimedia interactive networking, communications, streaming and interfacing over at least one wireless network.

20. The apparatus of claim 1, further comprising:
a location determination module configured to determine the precise location of the apparatus wrist mounted computing device, using the wireless network.

21. The apparatus of claim 20, further comprising:
a relational position and location determination system configured to identify precise location and relational position of the apparatus in relation to any of one or more wirelessly connected devices, sensors, objects or locations, using any of directional signal, signal strength and networked device location and spatial position data.

22. The apparatus of claim 19, wherein the apparatus is capable of uploading, downloading and streaming voice, data, video and multimedia content and real-time computing and interfacing on the Internet or other wired or wireless network.

23. The apparatus of claim 22, wherein the apparatus is configured for any of:
serving as a mobile hotspot to enable one or more wired or wirelessly networked devices to connect to the Internet or other wired or wireless network;
serving as a peer-to-peer wireless multimedia hub, for any of:
streaming voice, data, video and other multimedia content to one or more networked devices;
receiving voice, data, video and other multimedia content from a networked device; and
streaming content to one or more other networked devices, sensors or interfaces; or
serving as a networking hub and router for connecting one or more devices to a network of devices for shared data, multimedia content and/or interfacing.

24. The apparatus of claim 19, further comprising:
a signal receiving module for receiving data and position signals from one or more sensors mounted any of: on a body surface of the user, inside of the body of the user, on or embedded into clothing or equipment associated with the user, on a handheld device or object associated with the user, on an external person, device, vehicle, object or surface in the surrounding environment associated with the user, or on a remote networked person, device, vehicle, object or surface associated with the user.

25. The apparatus of claim 24, wherein the signal receiving module is configured for any of:
receiving data and position signals from multiple sensors mounted on, embedded in, or inside of a persons' body, clothing, equipment, device, vehicle or other object or surface the apparatus may generate 3D map of a person, object or other surface and map the spatial position, directional motion, velocity and acceleration of each surface and capture other collected sensor data; and
capturing full body motion and acceleration as a continuous data stream and assigning that data to a virtual model of the user to provide a real-time animation of the body enabling full body interfacing in a virtual and/or physical environment.

26. The apparatus of claim 24, further comprising:
a mesh sensor networking and mapping system;
wherein the apparatus is configured to operate as a sensor hub for a wireless sensor network (WSN), the apparatus being configured to network with each sensor directly or via a mesh network in which each sensor is configured to operate as a node or as a relay passing data on to the other nodes in the network; and
wherein the apparatus is configured to identify each sensor based on its assigned surface and map any of the 3-dimensional spatial position, directional motion, velocity, acceleration and other data collected by each sensor.

27. The apparatus of claim 19, further comprising:
a networked device interfacing system, wherein any of the apparatus the user can interface and control any of one or more remote networked devices, vehicles, objects or interfaces.

28. The apparatus of claim 1, further comprising:
a user verification module including any of:
light emitters, optical sensors, motion sensors, orientation sensors, location sensors, wireless sensors, electrical activity sensors and other sensors on the apparatus or networked with the apparatus for identifying and verifying the user, wherein the apparatus is configured to identify and verify the user using light and optical mapping, modeling and/or imaging of any of the hand, fingers and other body surfaces and verify the user based on any of their distinct joint, hand or body measurements, imaged hand, finger and other internal and external body surface data, electrical activity, heartbeat and other identifiers, hand prints, finger prints and/palm prints, eye imaging and face mapping and Identification.

29. The apparatus of claim 28, wherein the identifiable features associated with the user include any of: a hand, a finger, skin, muscles, veins, tendons, blood, heart rate, electrical activity, body mapping, modeling, imaging, hand motion, body motion, gestures, implanted sensors, ingested sensors or prosthetics.

30. The apparatus of claim 28, wherein the user verification module is configured to perform any of:
instant keyless user verification and authorization upon device sign-in;
instant user verification for any of payment and other secure transactions;
keyless entry to home and vehicles; and
access to any of unique user accounts, user specific functions, and applications on the apparatus; or
access to one or more networked devices, the Internet, or other networks.

31. The method of claim 1, further comprising a user verification module including any of:
light emitters, optical sensors, motion sensors, orientation sensors, location sensors, wireless sensors, electrical activity sensors and other sensors on the apparatus or networked with the apparatus for identifying and verifying the user, and wherein the apparatus is configured to monitor or detect one or more identifiable features associated with the user.

32. A method implemented with an apparatus that is wearable by a user, the method comprising:
with a processor housed in a housing module of the apparatus, communicating with light emitters and optical sensors housed in the housing module:
with an imaging system integrated within the apparatus, dynamically scanning one or more surfaces of any of:
at least a portion of the user's body,
an object held by the user,
an object near the user, or
at least a portion of an environment surrounding the user;
with the apparatus, acquiring the spatial position, direction motion, and orientation of the apparatus by any one or combination of onboard accelerometers, altimeters, compasses and gyroscopes, as well as GPS and radio frequency direction signal and location data to continuously identify the relation position of the apparatus, imaging system, light emitters and sensors to reflected and imaged surfaces to assign that data to each light point and color pixel in the scanned surfaces;
with the apparatus, dynamically mapping the spatial position of the scanned surfaces and the relational position of the projector to the scanned surface based on the acquired spatial position, direction motion, and orientation of the apparatus to dynamically determine the relational position of the imaging system to the dynamically imaged and/or mapped surfaces;
with one or more projecting devices integrated with the apparatus, dynamically projecting any of an undistorted image, an undistorted graphic user interface, or any combination thereof on the imaged and mapped surfaces, with the projectoring device(s), based on the dynamically determined relational position of the imaging system to the dynamically imaged and mapped surfaces.

33. The method of claim 32, wherein the processor is configured to interface with any of an external device, object or surface, wherein the interfacing comprises:
receiving gestural input of an interaction by the user with the projected image or graphic user interface on the scanned surfaces, utilizing at least one component of the imaging system;
determining any of touch and gestures performed by user, using a map of the surface of the body scan; and
transmitting predetermined signals to an external device based on the determined gesture.

34. The method of claim 33, wherein the interfacing with the external device includes:
determining the location of the apparatus using a position determination module; and
determining a specific device out of multiple possible devices to interface with based on the location of the apparatus and the map of the surface of the body scanned created by the processor.

35. The method of claim 34, wherein determining the location of the apparatus includes:

scanning surfaces, devices and objects in close proximity to the user; and processing data received in the scanning surfaces and objects to create a map of the environment around the user.

36. The method of claim 35, wherein the scanned surfaces, devices and objects in close proximity to the user comprise any of a body surface associated with the user, a device, object or surface ingested, implanted or inside of the user, assigned, attached or incorporated on or into clothing or equipment associated with the user, a wearable device associated with the user, a handheld device or object associated with the user, a device, object or other surface associated with an environment surrounding the user.

37. The method of claim 36, wherein a user interface is assignable to any of a device, object or other scanned surface associated with the user and the user's environment.

38. The method of claim 37, wherein the user interface is configured for controlling any of
- a projected display;
- the apparatus; or
- a paired or networked device, object, surface, screen or interface and/or a software program, or an application running on any of a networked device, or over a network.

39. The method of claim 32, wherein the surface mesh includes a plurality of vertices and a corresponding plurality of edges connecting the plurality of vertices, wherein each vertex in the plurality of vertices includes three coordinates.

* * * * *